(12) United States Patent
Stojanovic et al.

(10) Patent No.: US 9,243,024 B2
(45) Date of Patent: Jan. 26, 2016

(54) APTAMER-MEDIATED DRUG RELEASE

(75) Inventors: Milan N. Stojanovic, Fort Lee, NJ (US);
Renjun Pei, New York, NY (US);
Steven Michael Forna Taylor, Hackensack, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/245,201

(22) Filed: Sep. 26, 2011

(65) Prior Publication Data

US 2012/0114558 A1    May 10, 2012

Related U.S. Application Data

(63) Continuation of application No. PCT/US2010/028624, filed on Mar. 25, 2010.

(60) Provisional application No. 61/164,237, filed on Mar. 27, 2009.

(51) Int. Cl.
| | |
|---|---|
| *C07H 21/02* | (2006.01) |
| *A61K 31/70* | (2006.01) |
| *A61K 31/44* | (2006.01) |
| *A61K 31/7088* | (2006.01) |
| *A01K 67/00* | (2006.01) |

(52) U.S. Cl.
CPC ............ *C07H 21/02* (2013.01); *A61K 31/7088* (2013.01)

(58) Field of Classification Search
CPC .... C07H 21/00; C07H 21/02; A61K 31/7088; A61K 31/439
USPC .................... 536/23.1; 514/44, 279
See application file for complete search history.

(56) References Cited

U.S. PATENT DOCUMENTS

| | | | |
|---|---|---|---|
| 4,579,730 | A | 4/1986 | Kidron et al. |
| 5,204,108 | A | 4/1993 | Illum et al. |
| 5,915,378 | A | 6/1999 | Lloyd et al. |
| 7,300,922 | B2 * | 11/2007 | Sullenger et al. ........... 514/44 R |
| 7,375,088 | B2 | 5/2008 | Bachmann et al. |
| 8,084,204 | B2 | 12/2011 | Stojanovic et al. |
| 2004/0126762 | A1 | 7/2004 | Morris et al. |
| 2004/0203007 | A1 | 10/2004 | Stojanovic et al. |
| 2006/0172320 | A1 | 8/2006 | Stojanovic |
| 2007/0003906 | A1 | 1/2007 | Anderson |
| 2007/0111222 | A1 | 5/2007 | Chasin et al. |
| 2009/0099064 | A1 | 4/2009 | Lougheed |

FOREIGN PATENT DOCUMENTS

WO    WO 2010/088276    8/2010

OTHER PUBLICATIONS

Alexander, Cameron, "Stimuli-Responsive Hydrogels, Drugs take control", *Nature Materials*, 7: 767-768 (Oct. 2008).
Connor et al., "Insulin capture by an Insulin-linked Polymorphic Region G-quadruplex DNA Oligonucleotide", *J. Am. Chem. Soc.*, 128(15): 4986-4991, Apr. 19, 2006.
Salmaso et al., "Cyclodextrin/PEG based hydrogels for multi-drug delivery", *International Journal of Pharmaceutics*, 345(1-2): 42-50, Dec. 10, 2007.
Spencer et al., "Module 5: Organic Chemsistry Functional Groups", In: *Chemistry: Structure and Dynamics, 3rd Edition, John Wiley & Sons, Inc.* (online) 2005, (pp. 1-36) [retrieved on Jun. 15, 2010 from URL: <http://higheredbcs.wiley.com/legacy/college/spencer/047165552X/modules.mod5.pdf>].
Taylor et al., "Triggered release of an active peptide conjugate from a DNA device by an orally administrative small molecule", *Angew. Chem. Int. Ed.*, 48(24): 4394-4397 (2009).
Patel et al., "Structure, recognition and discrimination in RNA aptamer complexes with cofactors, amino acids, drugs and aminoglycoside antibiotics", *Reviews in Molecular Biotechnology*, 74: 39-60 (2000).
Famulok et al., "Functional Aptamers and Aptazymes in Biotechnology, diagnostics, and Therapy", *Chemical Reviews*, 107(9): 3715-3743 (2007).
Alexander, Stimuli-Responsive Hydrogels; Drugs take control. vol. 7 Oct. 2008, pp. 767-768, especially p. 767 col. 3, and p. 768, Col. 1, para. 1.
Spencer et al. Module 5: Organic Chemistry Functional Groups, in: Chemistry: Structure and Dynamics, 3rd Edition. John Wiley & Sons, Inc. (online) 2005, (retrieved on Jun. 15, 2010).
Taylor et al. Triggered Release of An Active Peptide Conjugate from DNA Device by an Orally Admistrable Small Molecule, Angewandte Chemie vol. 121 Issue 24, pp. 4458-4461 Published online May 8, 2009.
Patel et al. Structure, recognition and discrimination in RNA aptamer Complexes with Colactors, amino acids, drug and aminoglycoside antibiotics. Review in Molecular Biotechnology. 2000 vol. 74: pp. 39-60.
Famulok et al. Functional Aptamers and Aptazymes in Biotechnology, Diagnostics, and Therapy. Chemical Reviews, 2007 vol. 107, No. 9; pp. 3715-3743.
Sitaula, et al., "GOx signaling triggered by aptamer-based ATP detection", *Chemical Communications*, 48(74):9284-9286 (2012).
Shlyahovsky, et al., "Proteins modified with DNAzymes or aptamers act as biosensors or biosensor labels", *Biosensors & Bioelectronics*, 22(11):2570-2576 (2007).
Lyon, et al. "Interference studies with two hospital-grade and two home-grade glucose meters", *Diabetics Technology Ther.*, 11(10):641-647 (2009).
Mann, et al., "Accuracy of glucometers should not be assumed", *AmJ Crit Care*, 16(6):531-532 (2007).

(Continued)

*Primary Examiner* — Quang Nguyen
(74) *Attorney, Agent, or Firm* — Baker Botts L.L.P.

(57) ABSTRACT

Disclosed are aptamer/drug conjugate complexes and the use of such complexes, together with a trigger compound, to inducibly release a drug. Also disclosed are methods for establishing a drug reservoir in a subject using these complexes, whereby drug may be released as needed. One example of such a complex is an aptamer/insulin conjugate complex from which insulin may be released by an innocuous, orally administrable trigger, such as quinine.

18 Claims, 29 Drawing Sheets

(56) References Cited

OTHER PUBLICATIONS

Figure 1A:
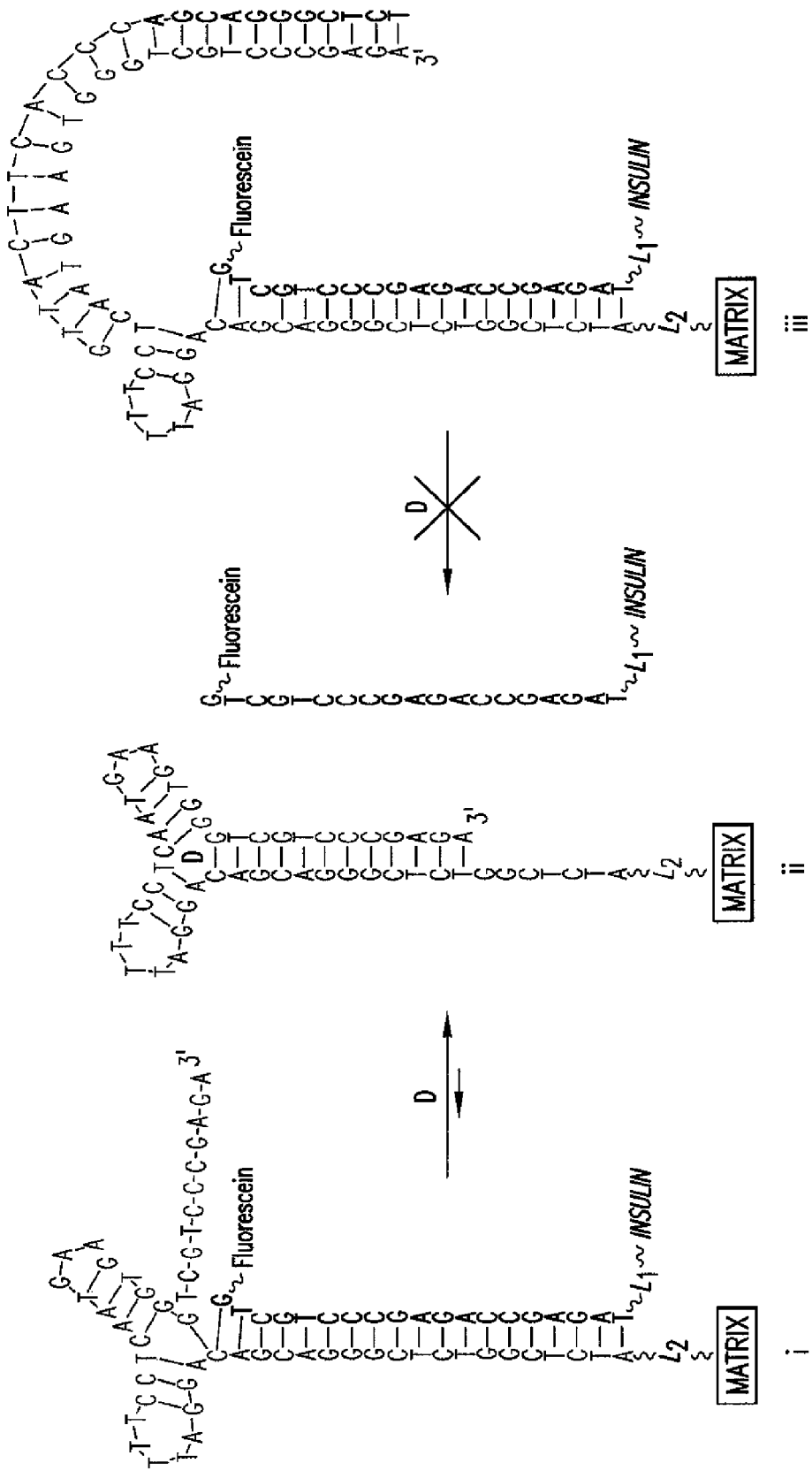

Deisingh, "Aptamer-based biosensors: biomedical applications", *Handb Exp Pharmacol.*, 173:341-357 (2006).
O'Sullivan, "Aptasensors—the future of biosensing?", *Anal. Bioanal chem.*, 372(1):44-48 (2002).
Wang, et al., "Aptamer-based fluorescent biosensors", *Curr Med Chem*, 18(27):4175-4184 (2011).
Famulok, et al., "Aptamer modules as sensors and detectors", *Ace Chem Res.*, 44(12):1349-1358 (2011).
Stojanovic, et al., "Modular aptameric sensors", *J Am Chem Soc.*, 126(30):9266-9270 (2004).
Walsh, "The rate of biopharmaceutical approvals has leveled off, but some milestones bode well for the future", Nat. *Biotechnol.* (2006), 24, 769-776.
Kumar et al., "Novel Devilery Technologies for Protein and Peptide Therapeutics", *Curr. Pharm. Biotechnol.* (2006), 7, 261-276.
Jarvis et al., "Biosimilars Bet", *Chem. Eng. News* (2009), 87, 28-29.
Polonsky et al., "Twenty-Four-Hour Profiles and Pulsatile Patterns of Insulin Secretion in Normal and Obese Subjects", *J. Clin. Invest.* (1988), 442-448.
Stojanovic et al., "Fluorescent Sensors Based on Aptamer Self-Assembly", *J. Am. Chem. Soc.* (2000), 122, 11547-11548.
Coffman and Dunn, "Insulin-Metal Ion Interactions: The Binding of Divalent Cations to Insulin Hexamers and Tetramers and the Assembly of Insulin Hexamers", *Biochemistry*, (1998), 27, 6179-6187.
Sorci et al., "Time-dependent insulin oligomer reaction pathway prior to fibril formation: Cooling and seeding" 2009, *Proteins* 77(1):62-73.
Chitta et al., 2006, "Application of SIMSTEX to Oligomerization of Insulin Analogs and Mutants", *J. Am. Soc. Mass Spectrometry* 17:1526-1534.
Brange et al., 1993, "Insulin Structure and Stability", *Pharm Biotech.* 5:315-350.
De Filippis et al., "Insulin Self-Association and the Relationship to Pharmacokinetics and Pharmacodynamics", 2001, *Crit. Rev. Therap. Drug Carrier Sys.* 18:201-264.
Markussen et al., "Immobilized Insulin for High Capacity Affinity Chromatography of Insulin Receptors", *J. Biol. Chem.* (1991), 266, 18814-18818.
Liu et al., "Glucose-Induced Release of Glycosylpoly(ethylene glycol) Insulin Bound to a Soluble Conjugate of Concanavalin A", *Bioconjugate Chem.* (1997), 8, 664-672.
Stojanovic et al., "Aptamer-Based Folding Fluorescent Sensor for Cocaine" *J. Am. Chem. Soc.*, (2001), 123, 4928-4931.
Wilson et al., "Functional Requirements for Specific Ligand Recognition by a Biotin-Binding RNA Pseudoknot" *Biochemistry*, (1998), 37, 14410-14419.
Sussan et al., "Preliminary Characterization of crystals of an in vitro evolved cyanocobalamin (vitamin B12) binding RNA", *Acta Crystallography* (1999), 55, 326-328.
Cho et al., "The Binding Site of a Specific Aminoglycoside Binding RNA Molecule", *Biochemistry* (1988), 37, 4985-4992.
Schurer et al., "Aptamers That Bind to the Antibiotic Moenomycin A", Bioorg. *Med. Chem.* (2001), 9, 2557-2563.
Kawazoe et al., "Extended in vitro selection for synthesis of novel molecular recognition oligonucleotide derivatives", *Nucl. Acids Symp. Ser.* (1992), 42, 177-178.
Kawazoe et al., "In Vitro Selection of Nonnatural Ribozyme-Catalyzing Porphyrin Metalation", *Biomacromolecules* (2001), 2, 681-686.
Lo et al., "A refillable microfabricated drug delivery device for treatment of ocular disease", *Lab on a Chip* (2008), 8, 1027.
Dittmer et al., "A DNA-Based Machine That Can Cyclically Bind and Release Thrombin", *Angew. Chem. Int. Ed.* (2004), 43, 3550-3553.
Kolpashchikov and Stojanovic, "Boolean Control of Aptamer Binding States", *J. Am. Chem. Soc.* (2005), 127, 11348-11351.
Nutiu and Li, "Structure-Switching Signaling Aptamers", *J. Am. Chem. Soc.* (2003), 125, 4771-4778.
Liu and Lu, "Fast Colorimetric Sensing of Adenosine and Cocaine Based on a General Sensor Design Involving Aptamers and Nonparticles", Angew. *Chem. Int. Ed.* (2006), 45, 90-94.
Rusconi et al., "RNA aptamers as reversible antagonists of coagulation factor IXa", *Nature* (2002), 419, 90-94.
Miyata et al., "A reversibly antigen-responsive hydrogel", *Nature* (1999), 399, 766-769.
Tang et al., "Aptamer Switch Probe Based on Intramolecular Displacement", *J. Am. Chem. Soc.* (2008), 130, 11268-11269.
Green et al. "A Rational Approach to Minimal High-Resolution Cross-Reactive Arrays", *J. Am. Chem. Soc.* (2006), 128, 15278-15282.
Franke et al., "Drug Monitoring of Quinine by HPLC in Cerebal Malaria with Acute Renal Failure Treated by Hacmofiltration", Eur. *J. Clin. Pharmocal.* (1987), 33, 293-296.
Hinds and Kim, "Effects of PEG conjugation on insulin properties", *Adv. Drug Delivery. Rev.* (2002), 54, 505-530.
Uchio et al., "Site-specific insulin conjugates with enhanced stability and extended action profile", *Adv. Drug. Delivery. Rev.* (1999), 35, 289-306.
Duckworth et al., "A Universal Method for the Preparation of Covalent Protein—DNA Conjugates for Use in Creating Protein Nanostructures", Angew. *Chem. Int. Ed.* (2007), 46, 8819-8822.
Wang et al., "Esterase 2-oligodeoxynucleotide conjugates as sensitive reporter for electrochemical detection of nucleic acid hybridization", *Bioelectron.* (2007), 22, 1798-1806.
J. G. McCormack, "Applying science to drug discovery", *Biochem. Soc. Trans.*, 34, 238 (2006).

\* cited by examiner

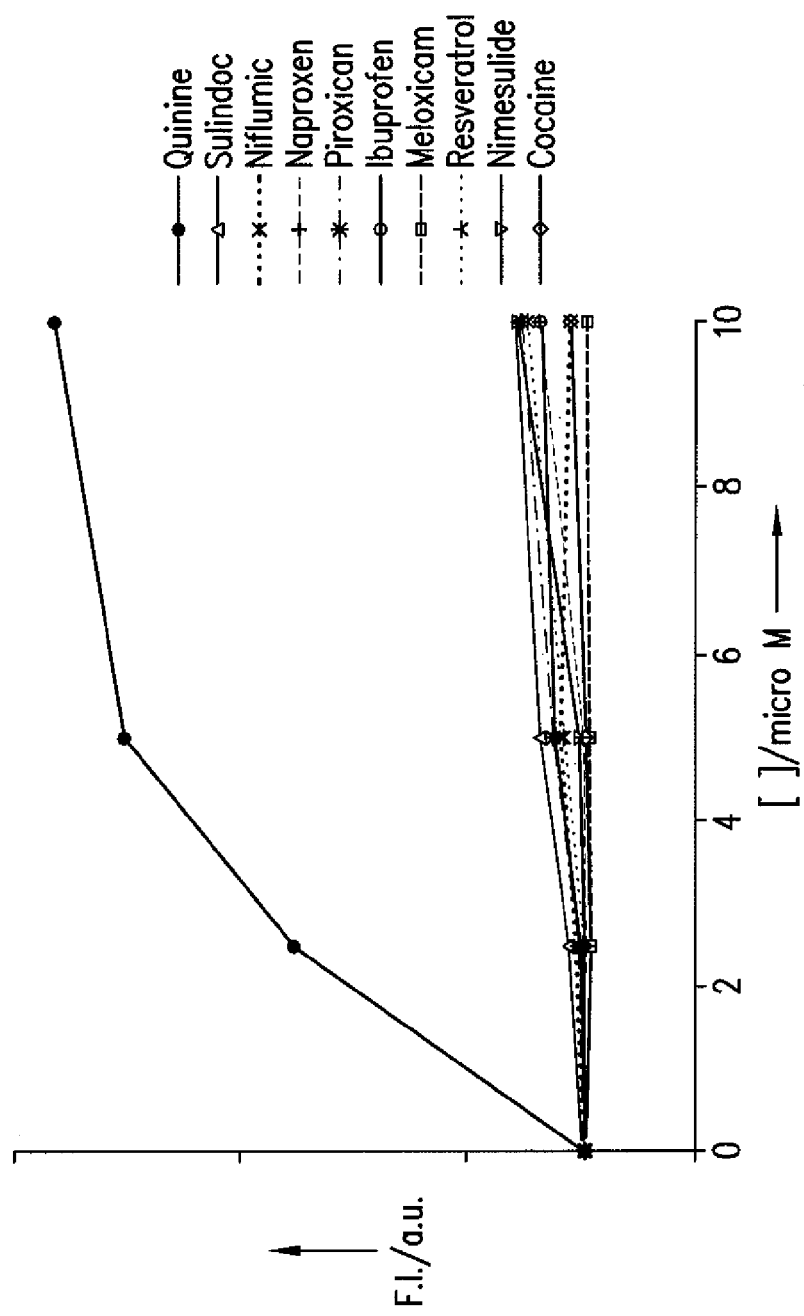
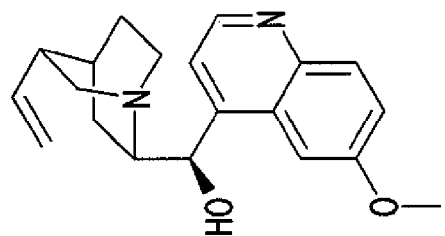
FIG.1B
FIG.1C

APTAMER-MEDIATED DRUG RELEASE

CROSS REFERENCE TO RELATED APPLICATIONS

The present application is a continuation of International Patent Application PCT/US10/028,624, filed Mar. 25, 2010, which claims priority to U.S. Provisional Application No. 61/164,237, filed Mar. 27, 2009, the contents of both of which are incorporated in their entireties by reference herein.

GRANT INFORMATION

This invention was made with government support under NSF CBC CHE-0533096, NSF EMT CCF-0621600, and NSF CCF-0726586 awarded by National Science Foundation. The government has certain rights in the invention.

1. INTRODUCTION

The present invention relates to aptamer/drug conjugate complexes and the use of such complexes, together with a trigger compound, to inducibly release a drug. Through these complexes, the present invention provides a means for establishing a drug reservoir in a subject, whereby drug may be released as needed. One specific embodiment of the invention provides an aptamer/insulin conjugate complex from which insulin may be released by an innocuous, orally administratable trigger, such as quinine.

2. BACKGROUND OF THE INVENTION

In recent years there has been a dramatic increase in the number of therapeutic peptides and proteins that have been approved for use or are in advanced clinical trails (Walsh, *Nat. Biotechnol.* (2006), 24, 769-776; Kumar et al., *Curr. Pharm. Biotechnol.* (2006), 7, 261-276; Jarvis et al., *Chem. Eng. News* (2009), 87, 28-29). Methods for their delivery are still primarily based on injectable formulations, often with inconvenient dosing regimes (Walsh, *Nat. Biotechnol.* (2006), 24, 769-776). For example, an important barrier to the ideal management of diabetes is a complex regimen of injections for insulin delivery, combining constant background (basal) release of insulin and increased dosages (bolus) after meals.

Accordingly, there is a need to provide a more convenient, less intrusive method of administering such therapeutic agents to patients, for example in the form of a molecular reservoir from which the therapeutic agent may be released as needed.

3. SUMMARY OF THE INVENTION

The present invention relates to aptamer/drug conjugate complexes from which drug conjugate may be released by an effective concentration of a trigger compound. It is based, at least in part, on the discovery that insulin, via a linked oligonucleotide tether, forms a complex with an aptamer, and that the insulin conjugate may be released by quinine in a concentration-dependent manner.

In certain non-limiting embodiments, the present invention provides for an aptamer/drug conjugate complex as well as its aptamer and drug conjugate components.

In related non-limiting embodiments, the present invention provides for a means of releasing drug conjugate from the aptamer/drug conjugate using a trigger. In a specific, non-limiting embodiment, the drug conjugate is insulin linked to an oligonucleotide tether. In further specific, non-limiting embodiments, the trigger is quinine.

In still further non-limiting embodiments, the present invention provides for a method of administering a drug to a subject comprising introducing, into the subject, an aptamer and a drug conjugate, wherein the aptamer and drug conjugate form a complex, and the drug may be administered to the subject by a trigger compound (trigger) which releases the drug conjugate from the complex and makes the drug available to the subject.

As one specific, non-limiting example, the present invention provides for a method of administering insulin to a diabetic subject, thereby treating diabetes. The inventive method may be used to substitute frequent insulin injections with oral administrations of trigger at meals to adjustably release an appropriate amount of insulin from the aptamer complex reservoir. Through better patient compliance, this regime could lead to improvement in both glycemic control and quality of day to day living.

4. BRIEF DESCRIPTION OF THE FIGURES

FIG. 1A-C. (A) A DNA device for small molecule triggered release of insulin, where D is a small molecule drug: Equilibrium shifts from (i) to (ii) in the presence of D; Note that triggering can be blocked with an inhibitor oligonucleotide (blue strand of complex (iii)). (B) Screening results for binding of FDA approved drugs to the aptamer MNS-1. (C) Structure of quinine. The sequence of the DNA device used herein is Matrix-$L_2$-ATC TCG GTC TCG GGA CGA CAG GAT TTT CCT CAA TGA AGT GGG TCG TCC CGA GA-3' (SEQ ID NO:8). The sequence of the insulin conjugate used herein is Fluorescein-5'-GTC GTC CCG AGA CCG AGA T-3'-$L_1$-Insulin (SEQ ID NO:9). The sequence of the inhibitor oligonucleotide used herein is 5'-TCT CGG GAC GAC CCA CTT CAT TG-3' (SEQ ID NO:10).

Figure 2A:
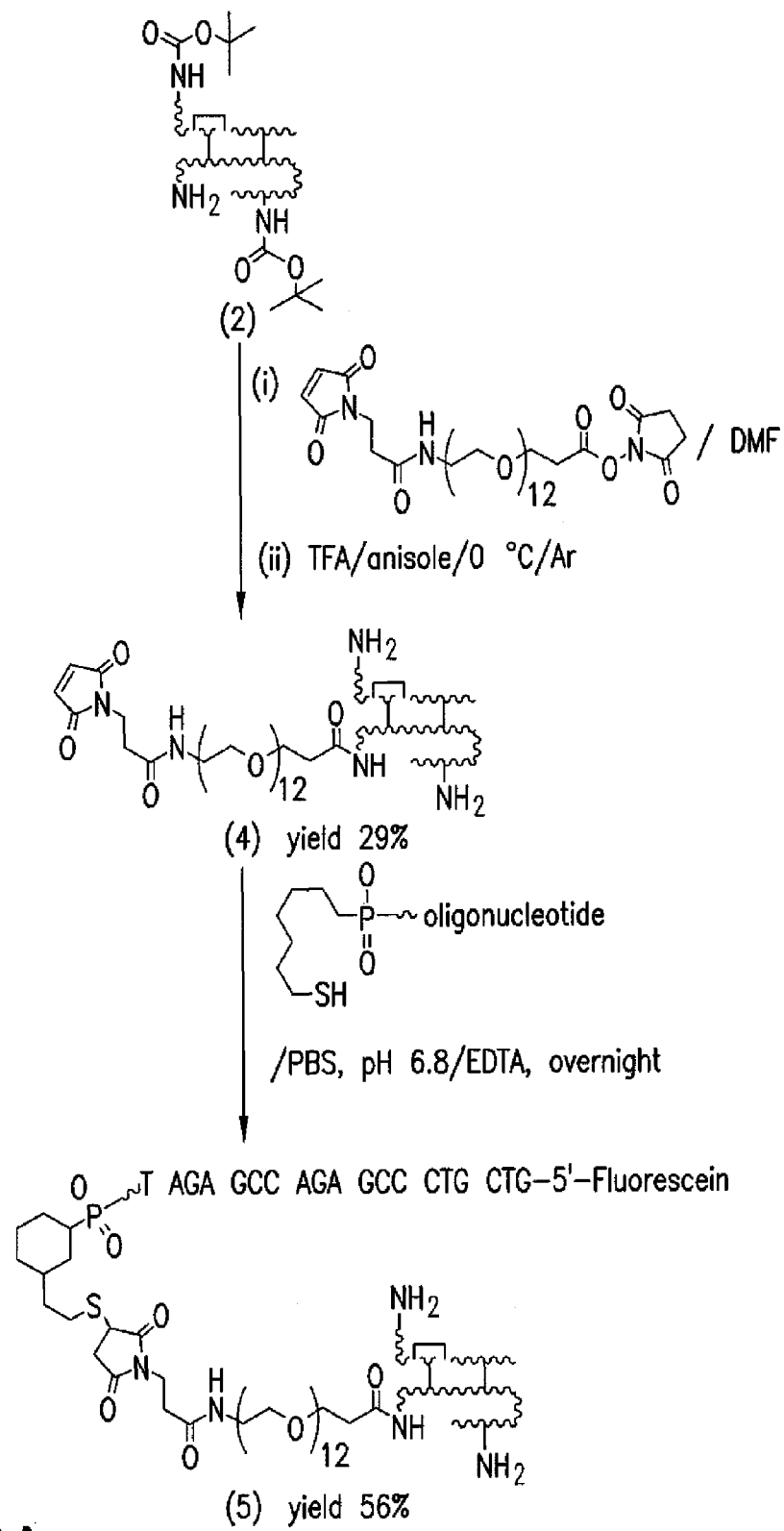
Figure 2B:
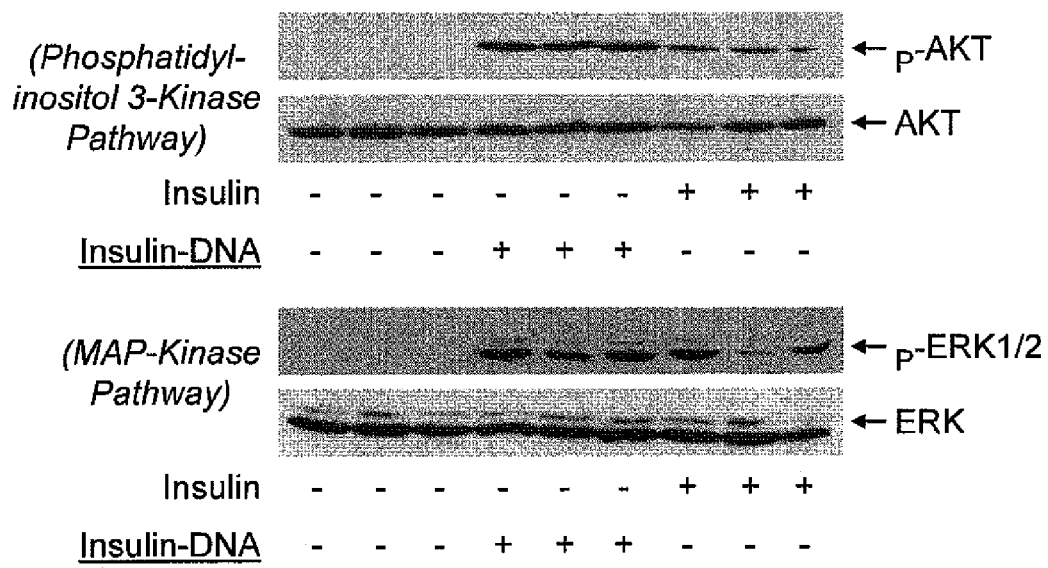

FIG. 2A-B. (A) Synthesis of the insulin-oligonucleotide conjugate Fluorescein-5'-GTC GTC CCG AGA CCG AGA T-3'-L1-Insulin (SEQ ID NO:9) (insulin represented as two chains displaying three amino groups (two protected) (2) (HPLC yields provided). (B) Effects of insulin-oligonucleotide conjugate on rat hepatoma cell insulin signaling pathways (in triplicate).

FIG. 3A-D. Surface plasmon resonance results—first derivative plots which showed the amount of insulin-conjugate released per time period. µM concentrations referred to [quinine], and asterisk (*) indicated that 1 µM inhibitor was added. (A) Three insulin-conjugate boluses produced by escalating concentrations of quinine. The solid and dotted-line traces represented reproducible release of conjugate at 0, 2, and 8 µM quinine after reloading of matrix. The dashed-line trace represented release with 0, 1, and 8 µM quinine demonstrating the use of quinine concentration to control the amount of the second bolus. (B) Inhibitor added preventing release of insulin conjugate in the presence of quinine—solid-line trace (compared with dotted-line trace, i.e. same experiment but without inhibitor added), —profile of release of insulin-conjugate when quinine is not added—dashed-line trace. (C) Three insulin-conjugate boluses produced by 1.5, 6, and 18 µM quinine. (D) Typical human serum levels of insulin over a 24 hour period—in response to meals at 9:00 AM, 1:00 PM and 6:00 PM adapted from Polonsky et al., *J. Clin. Invest.* (1988), 81, 442-448.

Figure 4:
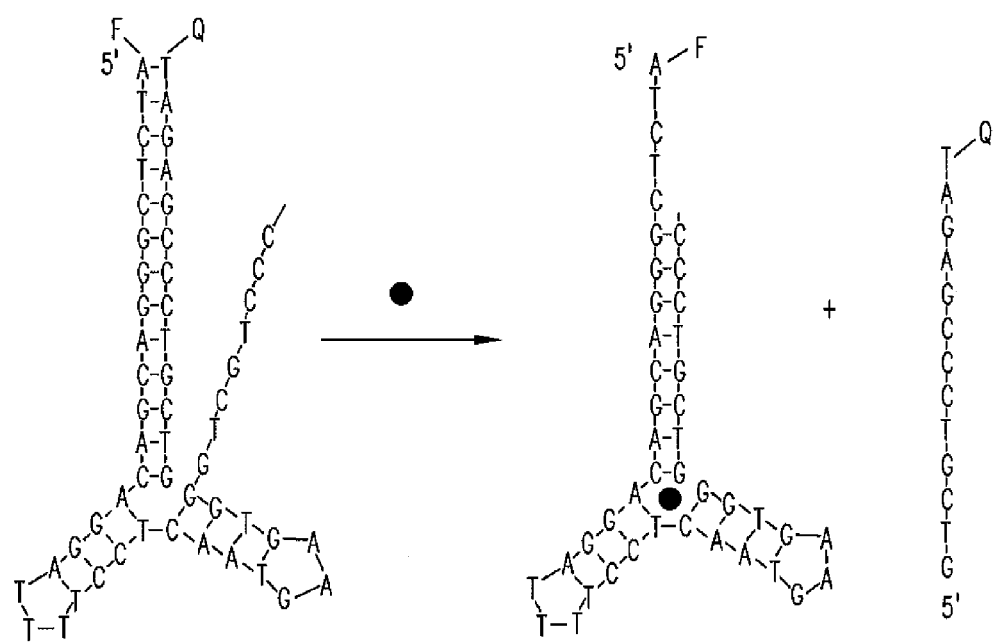

FIG. 4. The cocaine aptamer MNS-1 (Stojanovic et al., *J. Am. Chem. Soc.* (2000), 122, 11547) used for screening for tight binding FDA drugs (●). It shows a complex comprising oligonucleotides 5'-ATC TCG GGA CGA CAG GAT TTT CCT CAA TGA AGT GGG TCG TCC C-3' (SEQ ID NO:1) and 5'-GTC GTC CCG AGA T-3' (SEQ ID NO:2).

Figure 5:
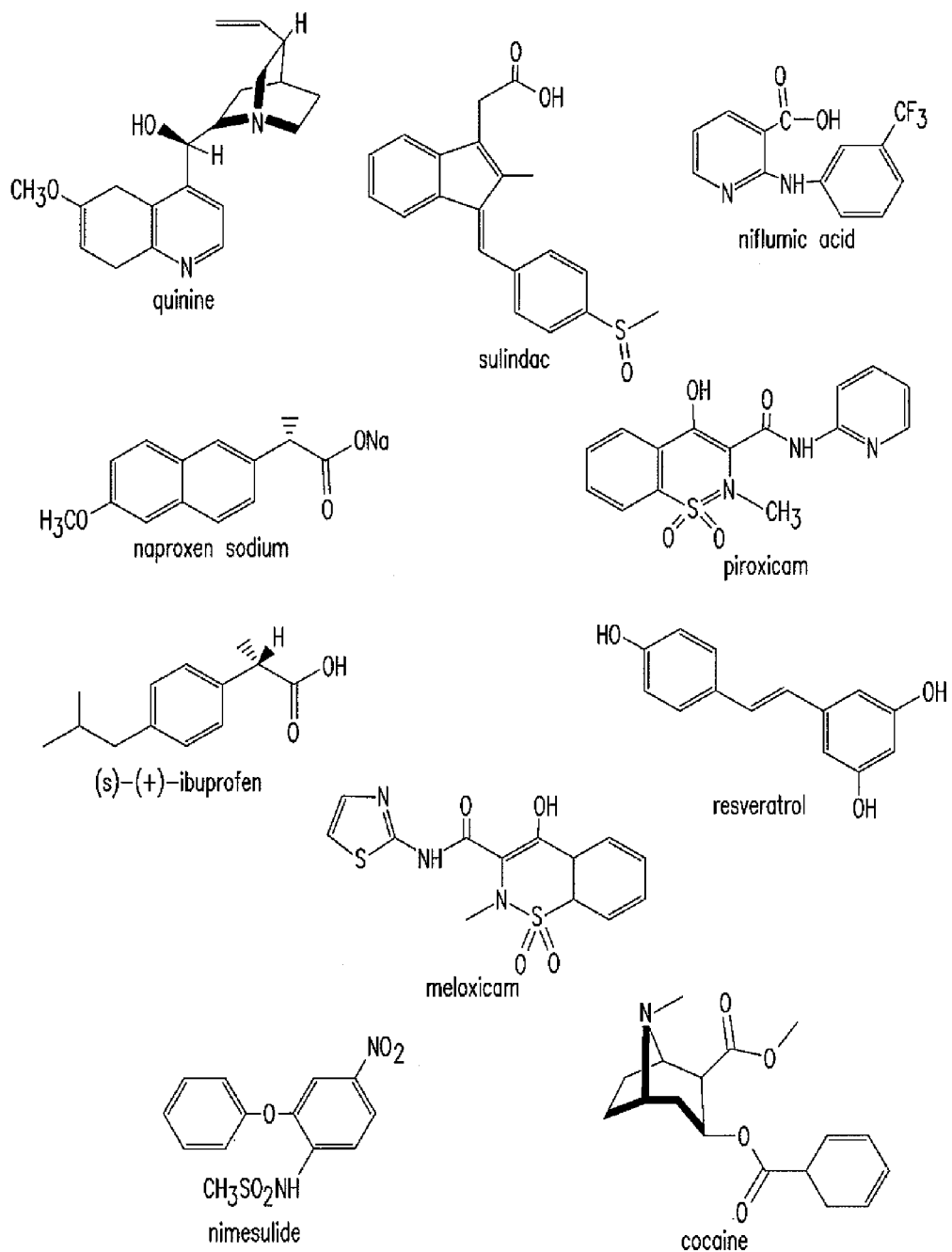

FIG. 5. FDA approved drugs screened against MNS-1 "cocaine aptamer."

Figure 6A:
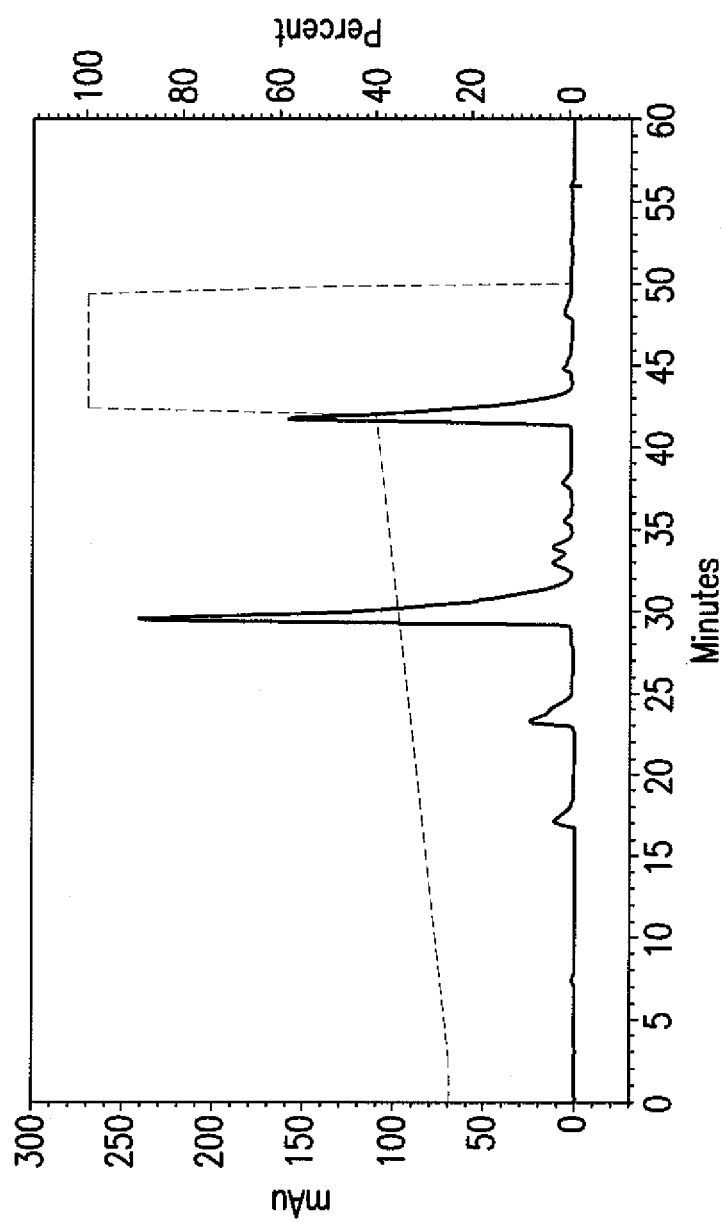
Figure 6B:
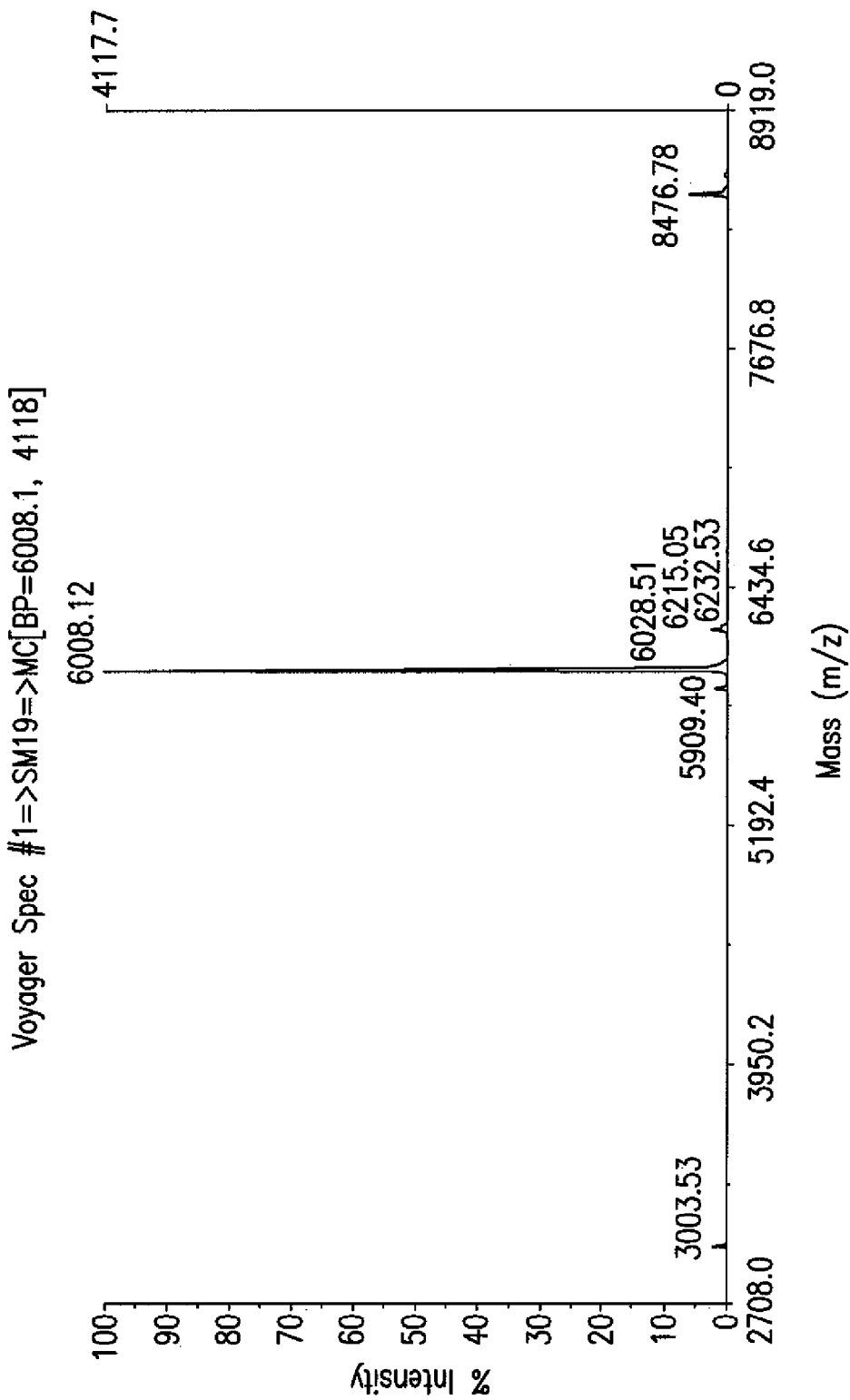

FIG. 6A-B. (A) A reverse phase chromatography trace of the crude reaction mixture showing DI (2) as the major peak. Buffer A was composed of 0.25% acetic acid, and buffer B 0.25% acetic acid in 90% acetonitrile. The gradient run is shown by the dotted line (right y-axis). A total flow rate of 5 mL min$^{-1}$ was used. (B) MALDI-TOF mass spectrum of isolated DI (2)

Figure 7:
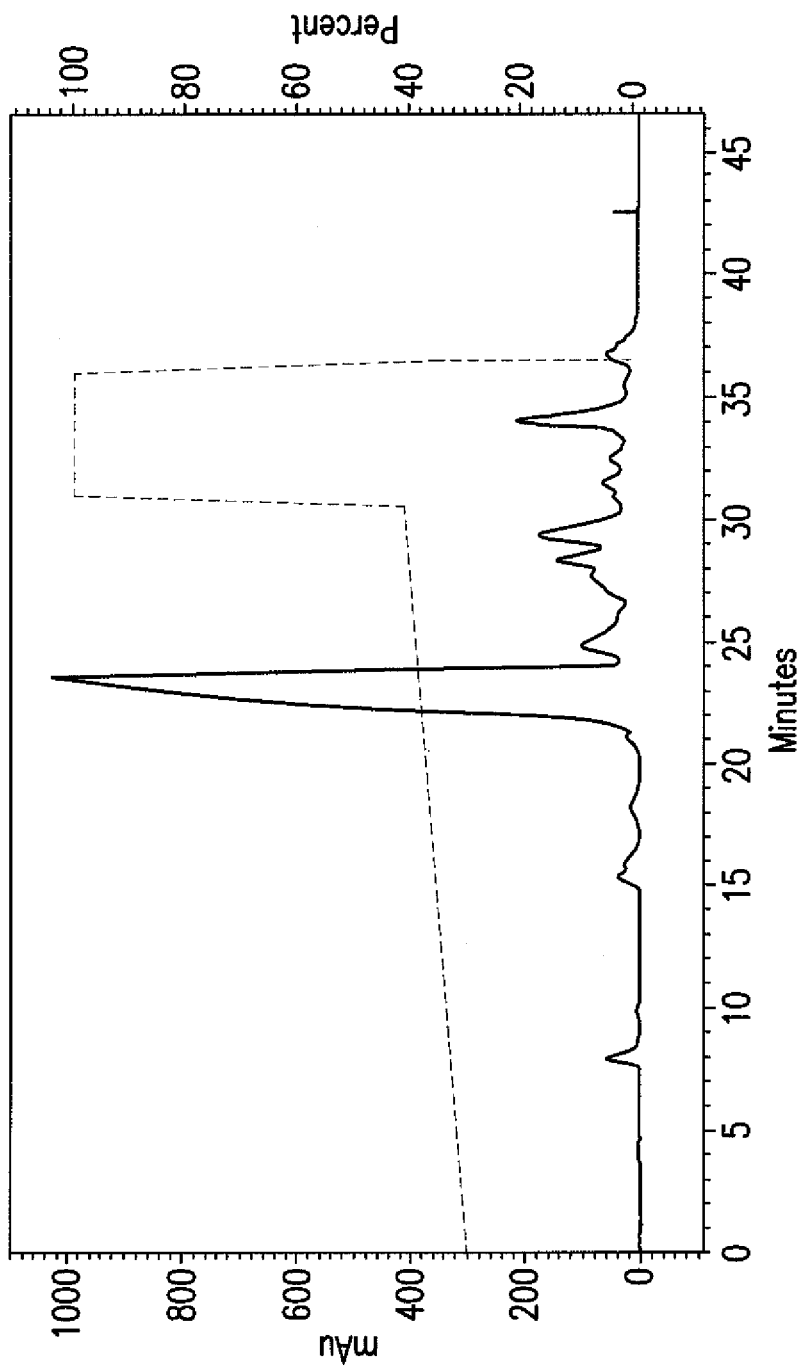

FIG. 7. A reverse phase chromatography trace of the crude reaction mixture showing DI-PEO$_{12}$-M (3) as the major peak. Buffer A was composed of 0.25% acetic acid, and buffer B 0.25% acetic acid in 90% acetonitrile. The gradient run is shown by the dotted line (right y-axis). A total flow rate of 5 mL min$^{-1}$ was used.

Figure 8A:
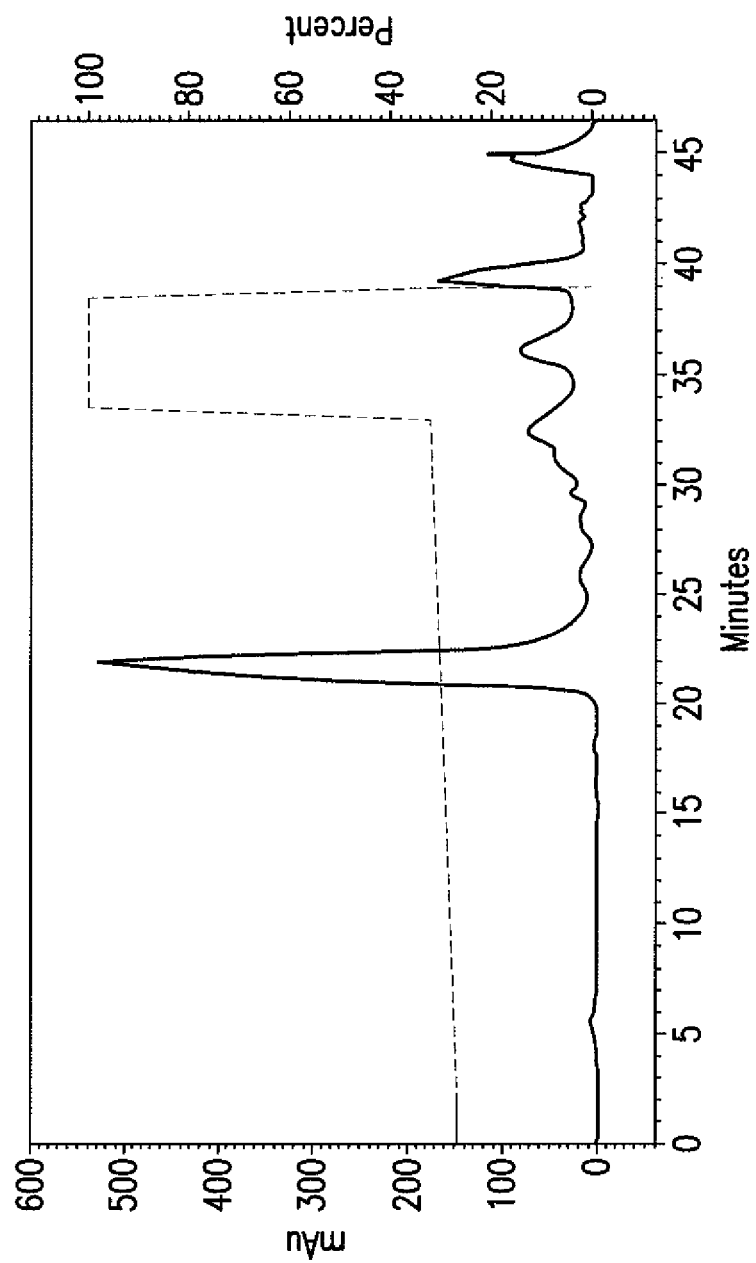
Figure 8B:
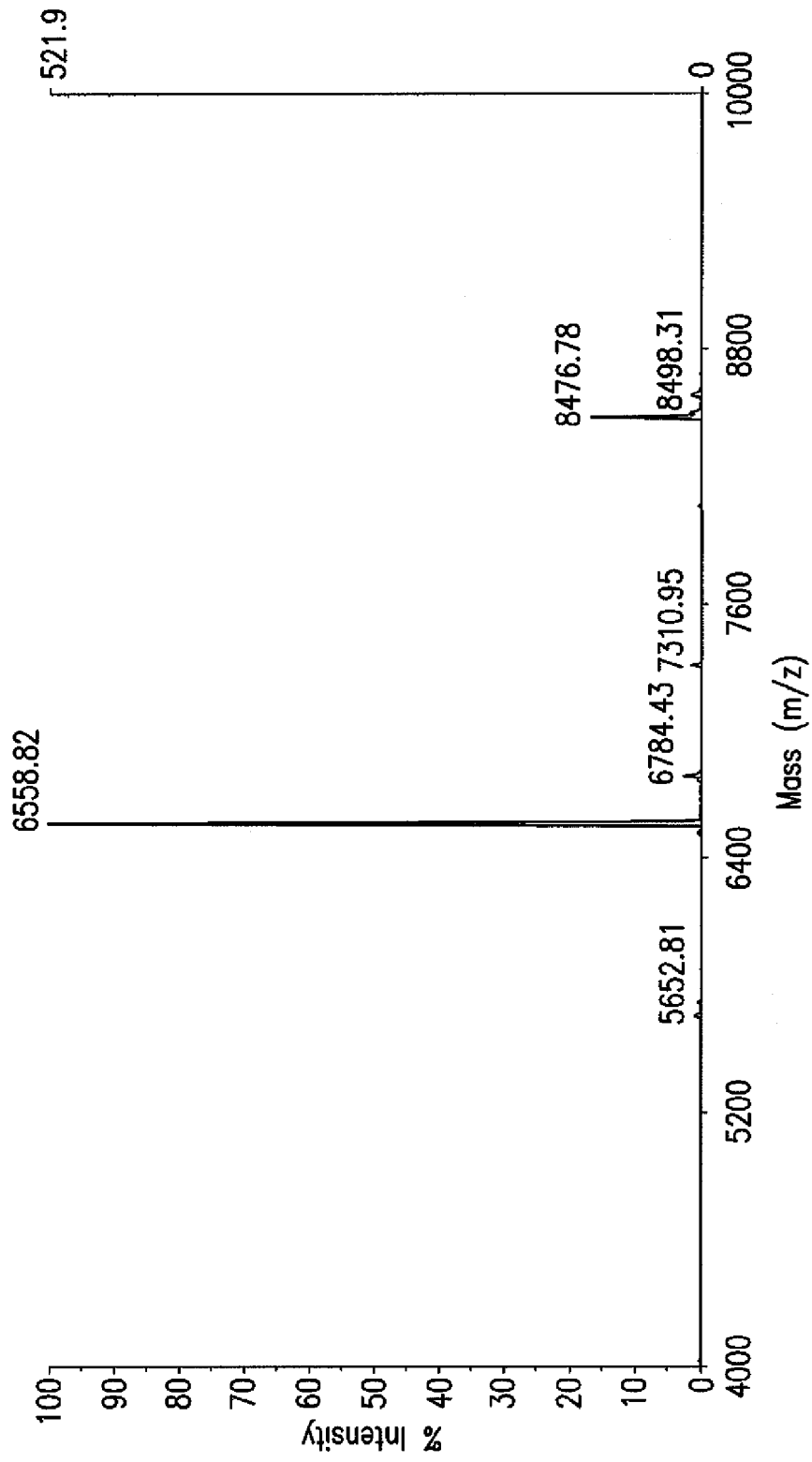

FIG. 8A-B. (A) A reverse phase chromatography trace of the crude reaction mixture showing I-PEO$_{12}$-M (4) as the major peak. Buffer A was composed of 0.25% acetic acid, and buffer B 0.25% acetic acid in 90% acetonitrile. The gradient run is shown by the dotted line (right y-axis). A total flow rate of 5 mL min$^{-1}$ was used. (B) MALDI-TOF mass spectrum of isolated I-PEO$_{12}$-M (4).

Figure 9A:
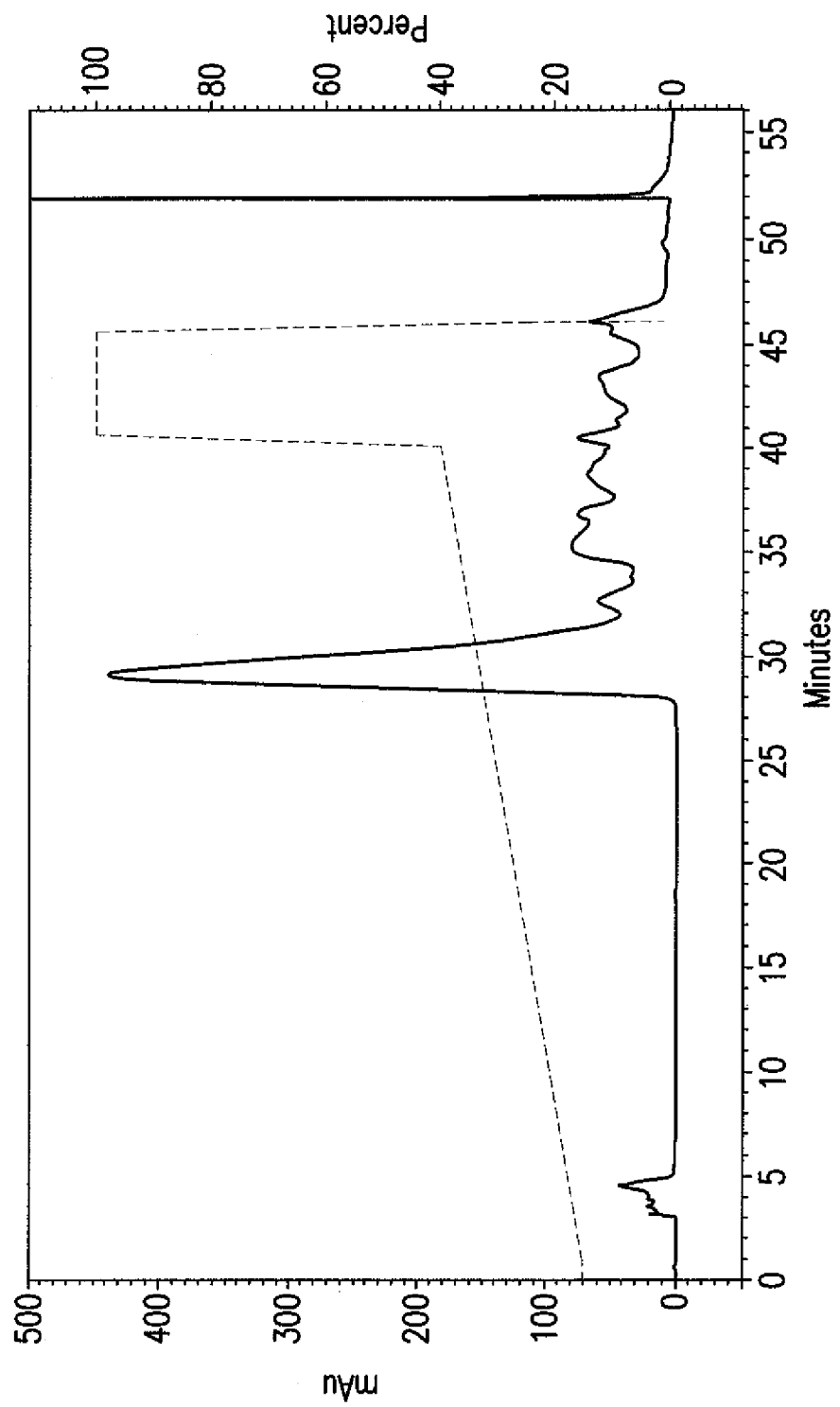
Figure 9B:
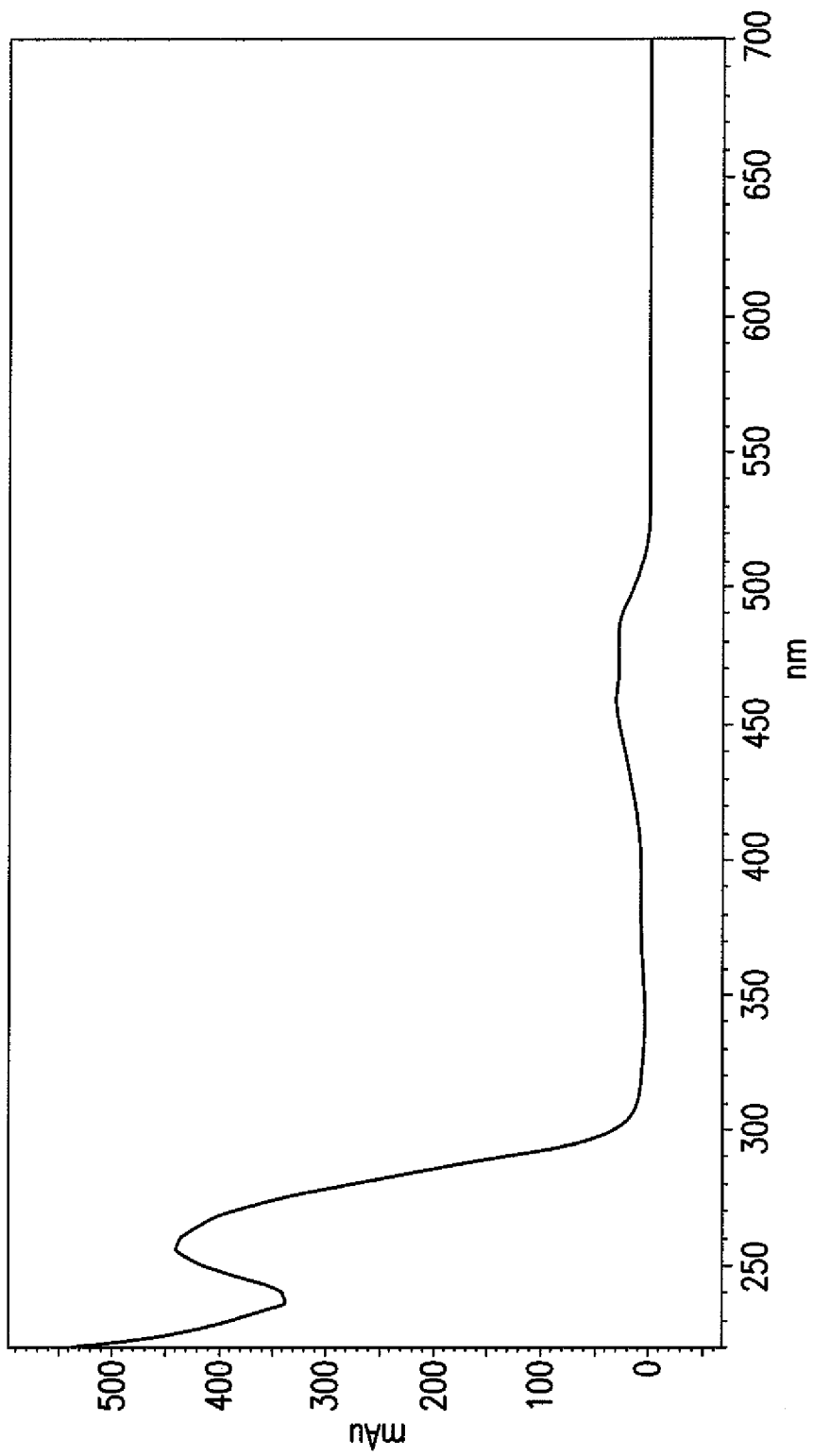

FIG. 9A-B. (A) A reverse phase chromatography trace of the crude reaction mixture showing I-PEO$_{12}$-InsLongF (5) as the major peak. Buffer A was composed of 0.05% LiClO$_4$, and buffer B 0.05% LiClO$_4$ in 90% acetonitrile. The gradient run is shown by the dotted line (right y-axis). A total flow rate of 5 mL min$^{-1}$ was used. (B) Major product from FIG. 9A, i.e. (5).

Figure 10:
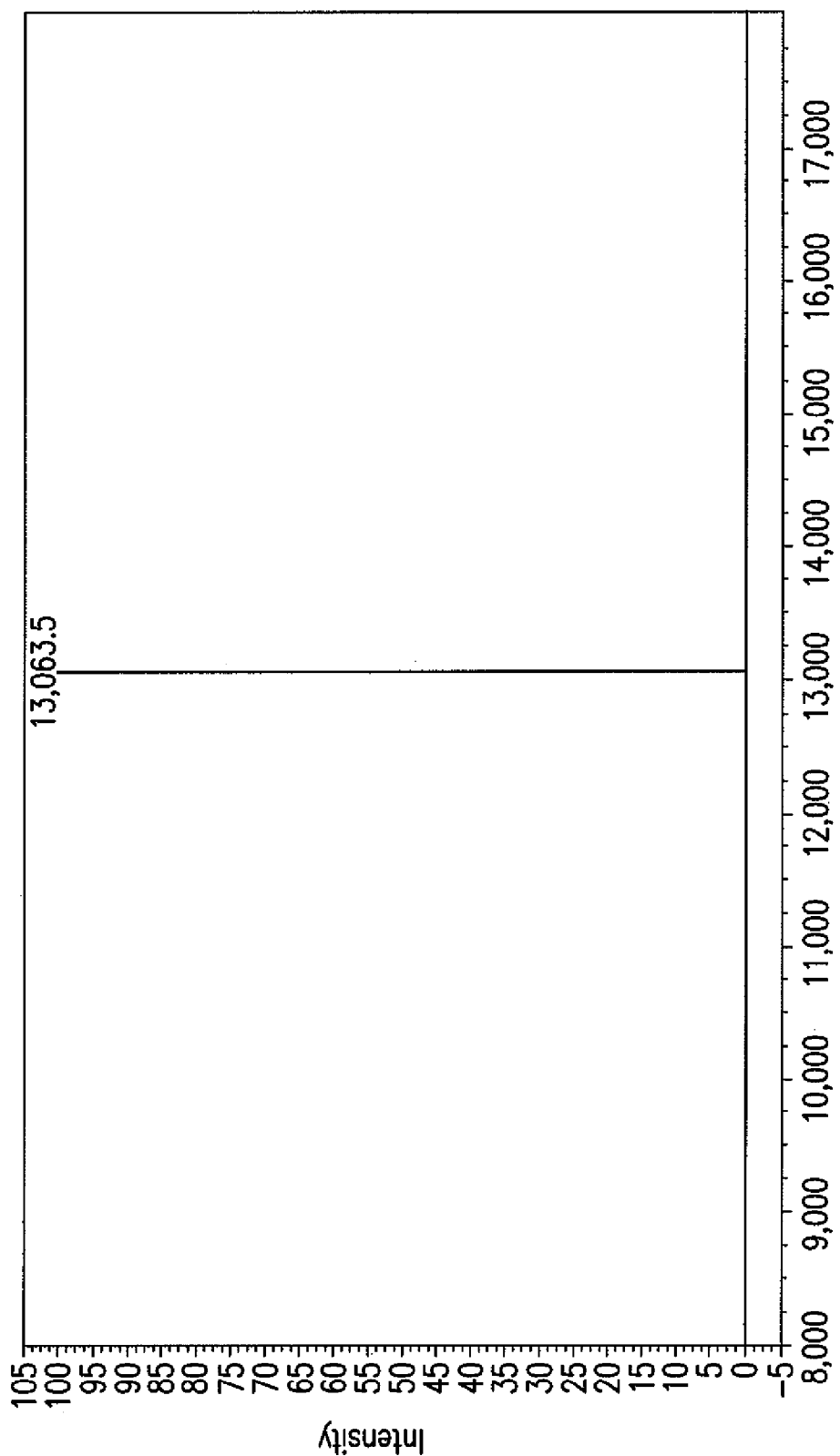

FIG. 10. Major product from FIG. 9A, i.e. (5). Mass spectrum carried out by IDT (Coralville, Iowa) on a Novatia HTCS-2K system with ProMass software. The Deconvolution Report is shown in Table 1 below.

TABLE 1

Deconvolution Report

| Mass (Da) | +−Std. Dev. | Intensity | Score | Delta Mass | % Relative | % Total |
|---|---|---|---|---|---|---|
| 13063.5 | 0.3 | 5.32E+007 | 5.72 | 0.0 | 100.0 | 99.7 |
| 13105.1 | 1.0 | 1.48E+005 | 6.10 | 41.6 | 0.3 | 0.3 |

Figure 11:

FIG. 11. 20% Native PAGE at 150 Volts for 50 minutes in TRIS-Glycine running buffer. Left is oligonucleotide, right is insulin-oligonucleotide conjugate (5), stained with SYBR-GOLD (Invitrogen).

Figure 12A:
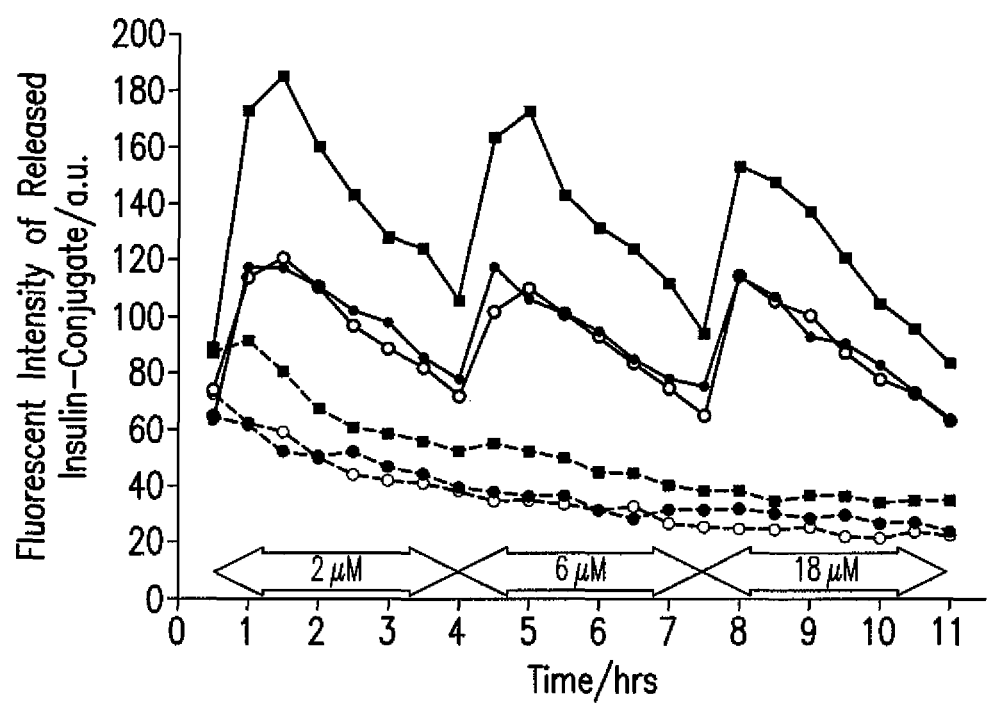
Figure 12B:
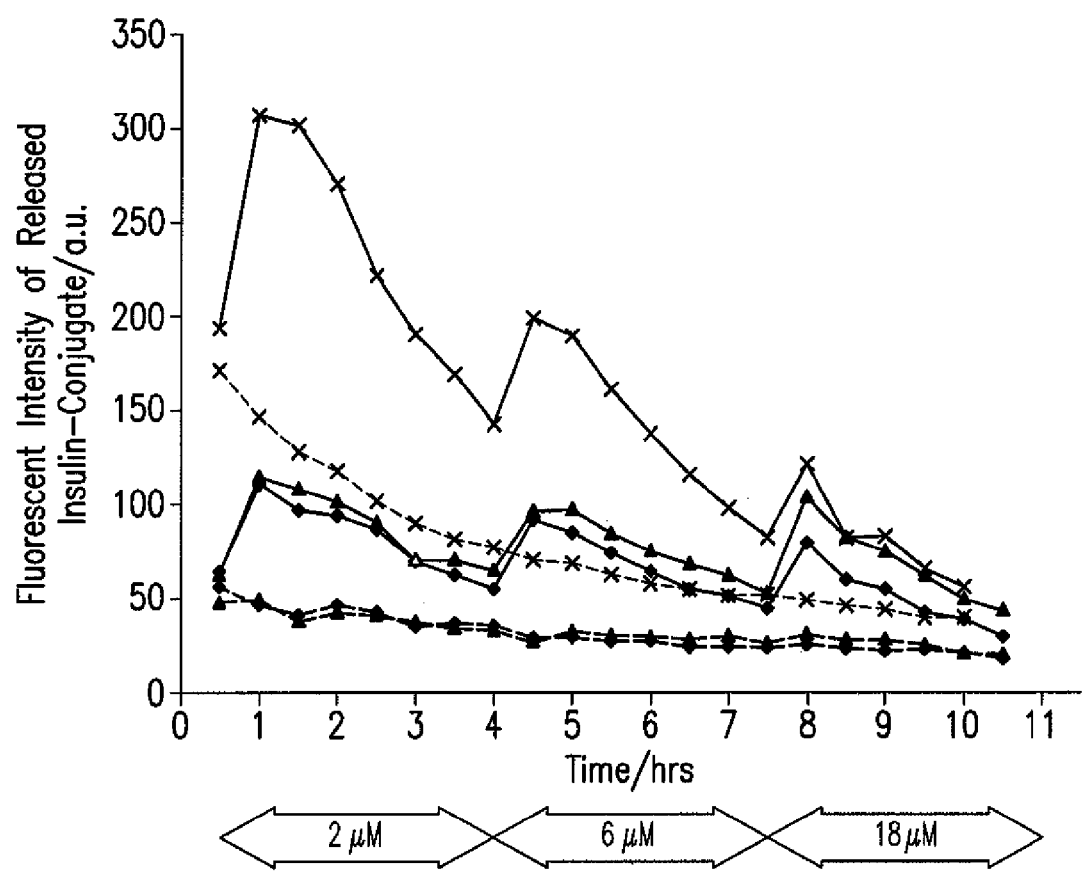

FIG. 12A-B. Traces (solid lines) showing three quinine triggered release of insulin-conjugate (5) from microspheres (with negative control (dotted line), i.e. no exposure to quinine in the same symbol). The first pulse (first peak) was triggered with 2 µM quinine, the second pulse with 6 µM, and the third pulse with 18 µM quinine. Traces marked with squares, open circles and closed circles are repeats of five-fold diluted surfaces (i.e. an average of one aptamer per biotin binding site), which were prepared by heating microspheres loaded with quinine aptamer and insulin-oligonucleotide conjugate at 70° C. for 15 minutes before incubation overnight at room temperature (see above for hybridization conditions). Note that the optimal system for quinine release from microspheres differed in the aptamer oligonucleotide by two additional base pairs when compared with the optimal sequence for the Biacore experiments. The sequence of the aptamer used for the microsphere experiments was 5'-/5BioTEG//iSp18//iSp18/ATC TCG GTC TCG GGA CGA CAG GAT TTT CCT CAA TGA AGT GGG TCG TCC CGA GA<u>C C</u>-3' (SEQ ID NO:7) (additional bases, relative to Biacore experiments, denoted by underscore). (B) Quinine triggered release of insulin-conjugate (5) from microspheres (solid lines), (negative control (dotted lines), i.e. no exposure to quinine is shown by a line marked with the same symbol). The first pulse was triggered with 2 µM quinine, the second pulse with 6 µM, and the third pulse with 18 µM quinine. The trace marked with triangles represents results after heating the microspheres, loaded with quinine aptamer and insulin-oligonucleotide conjugate, at 70° C. for 15 minutes before incubation overnight at room temperature; the trace marked with diamonds represent results where microspheres were saturated with aptamer and not heated. The trace marked with X's represents release of the oligonucleotide portion of the insulin-oligonucleotide conjugate, i.e. bare oligonucleotide—no insulin attached, prepared under the same conditions as the experiments shown in FIG. 12A. Note that the fluorescence intensity was c.a. 2-fold greater for the oligonucleotide over the insulin-oligonucleotide conjugate at the same concentration, which should be taken into account if comparing relative amounts released from the microsphere.

Figure 13A:
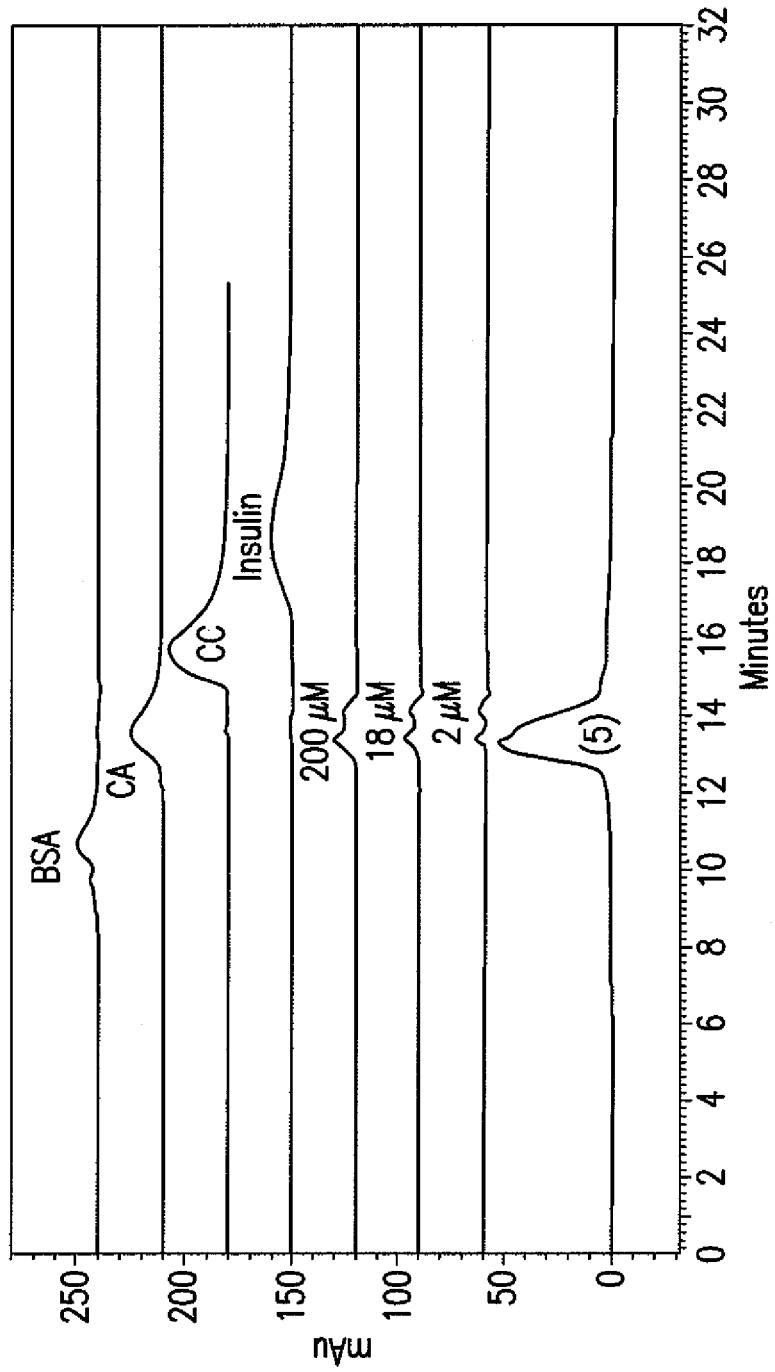
Figure 13B:
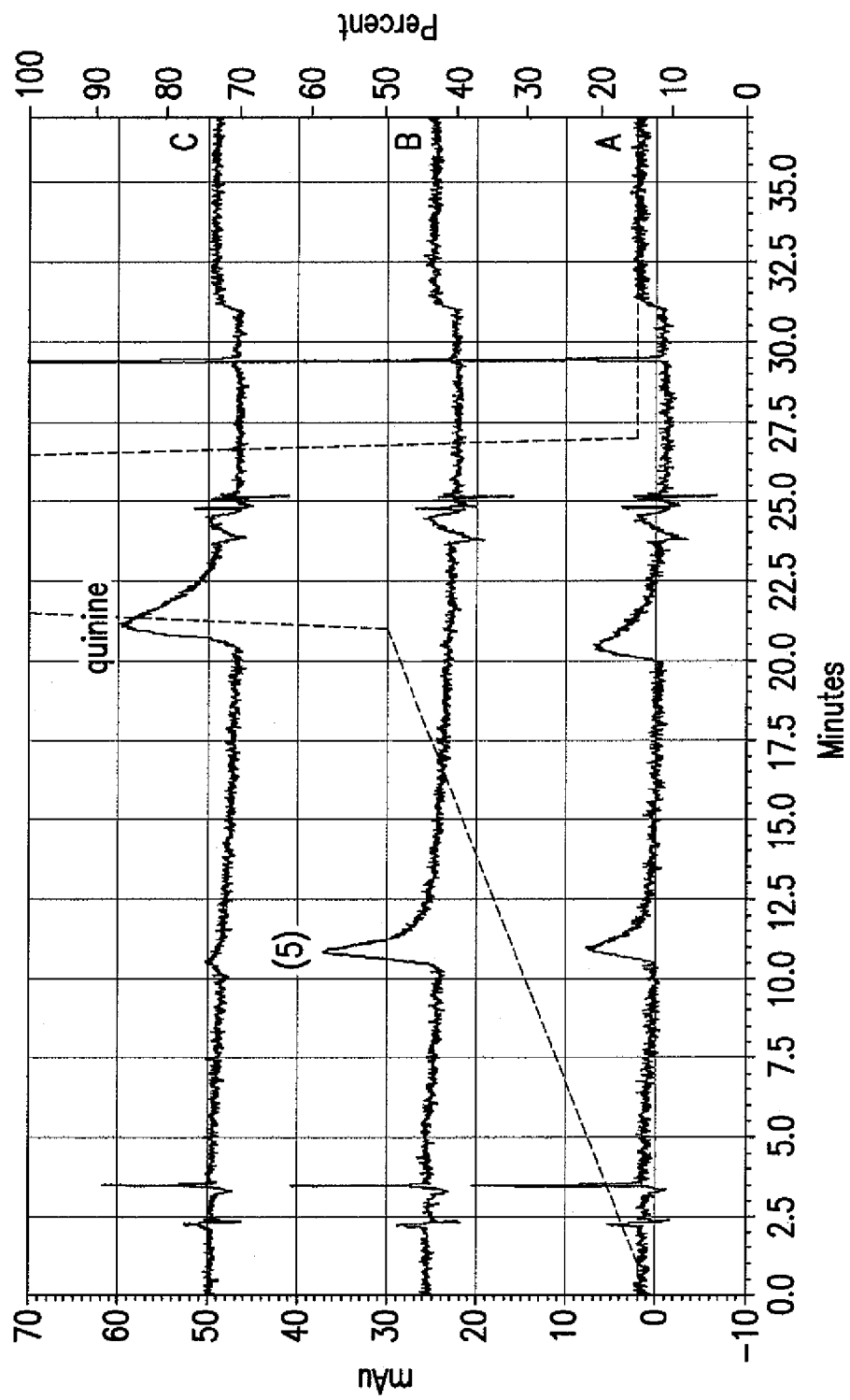

FIG. 13A-B. (A) Size exclusion chromatography of released oligonucleotide conjugate (5) (13 kD) from microspheres in the presence of 2, 18, and 200 µM quinine, obtained on a Zorbax® GF-250 column (Analytical 9.4×250 mm, 4-Micron), eluting with 20 mM TRIS, 1M NaCl, pH 7.4 buffer, at 30° C. BSA (bovine serum albumin, 66 kD), CA (carbonic anhydrase, 29 kD), and CC (cytochrome c, 12.4 kD) are protein ladder standards. Native insulin (5.5 kD) was also included. Note that (5) was non-globular, accounting for deviation from the protein ladder standards. The two peaks observed for all insulin-conjugate samples were assigned to the monomer and dimer (Coffivan and Dunn, *Biochemistry*, (1998), 27, 6179). The experiment supported that what was released from the microsphere on addition of quinine was the conjugate (5), as shown by the lowest trace (conjugate before application) compare with the 2, 18 and 200 µM traces directly above it—product released form the microsphere). (B) Reverse phase HPLC chromatography: A) of released oligonucleotide conjugate (5) from microspheres in the presence of 200 µM quinine (incubated over the weekend); B) Conjugate (5) before applied to microspheres; C) 200 µM only, note that (5) appeared as a 'ghost peak' (an artifact) in this trace due to the sample for "C" being immediately injected following sample "B"). Obtained on an Alltech Kromasil C18 10u column (Length 250 mm, ID 4.6 mm) (Lot No. DT0247, Part No. 62648), eluting with water (Buffer A)/90% acetonitrile in water (buffer B) (both buffers containing 0.05% LiClO$_4$) according to the gradient shown in the Figure above (dashed line, right hand y-axis is % buffer B). The experiment supported that the identity of the product released from the microspheres on addition of quinine was that of the conjugate (5).

Figure 14:
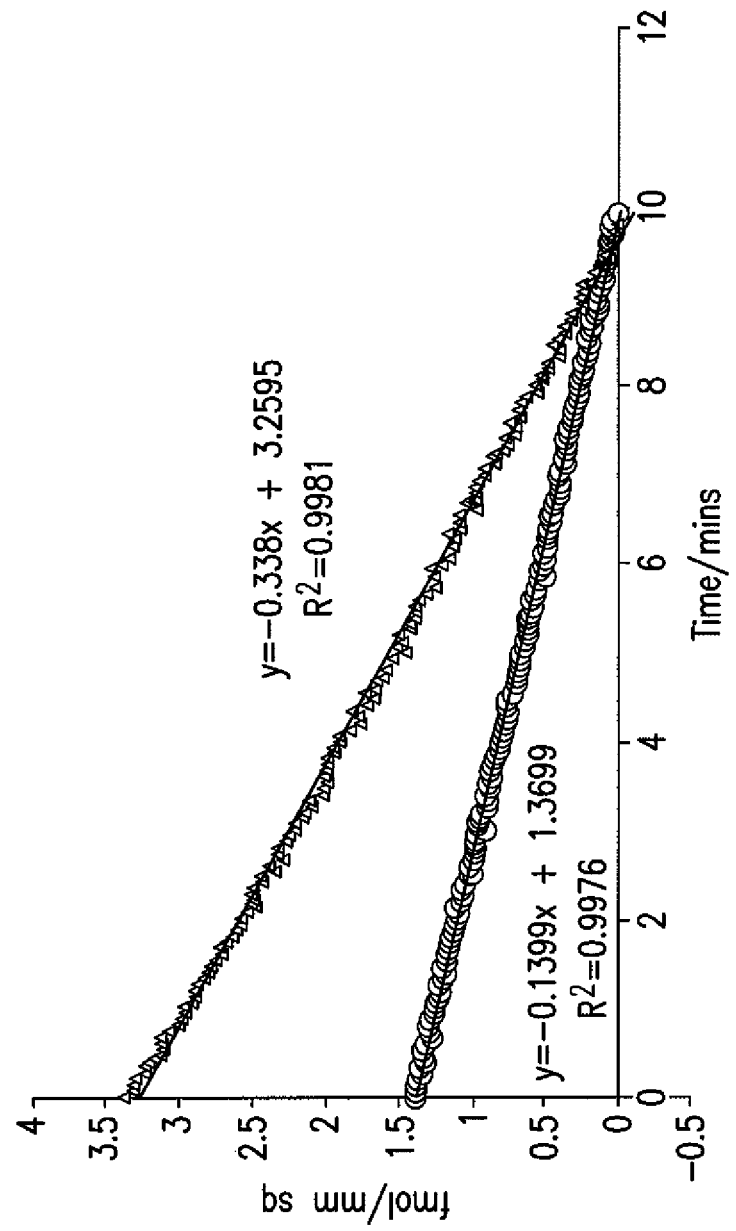

FIG. 14. Initial rate data for the dissociation of oligonucleotide (Δ) and insulin-conjugate (○) from an SA chip (Biacore). The line of best fit slope was equal to −0.338 fmol mm$^{-2}$ min$^{-1}$ for the oligonucleotide and −0.1399 fmol mm$^{-2}$ min$^{-1}$ for the conjugate. Note that the data was fitted to a straight line from 15 minutes to 25 minutes for both sets. It is mechanistically interesting that the optimal system for the insulin-conjugate release was sub-optimal for release of the oligonucleotide itself (i.e., without insulin attached). The oligonucleotide was rapidly released on its own, or with a single bolus of quinine, indicating that the insulin moiety significantly slows the release of the conjugate, possibly due to insulin-insulin interactions (Coffman and Dunn, *Biochemis-* try (1988), 27, 6179-6187) (e.g., the observed initial dissociation rate for the insulin conjugate was 0.14 fmol mm$^{-2}$ min$^{-1}$, and for the oligonucleotide alone was 0.34 fmol mm$^{-2}$ min$^{-1}$).

Figure 15A:
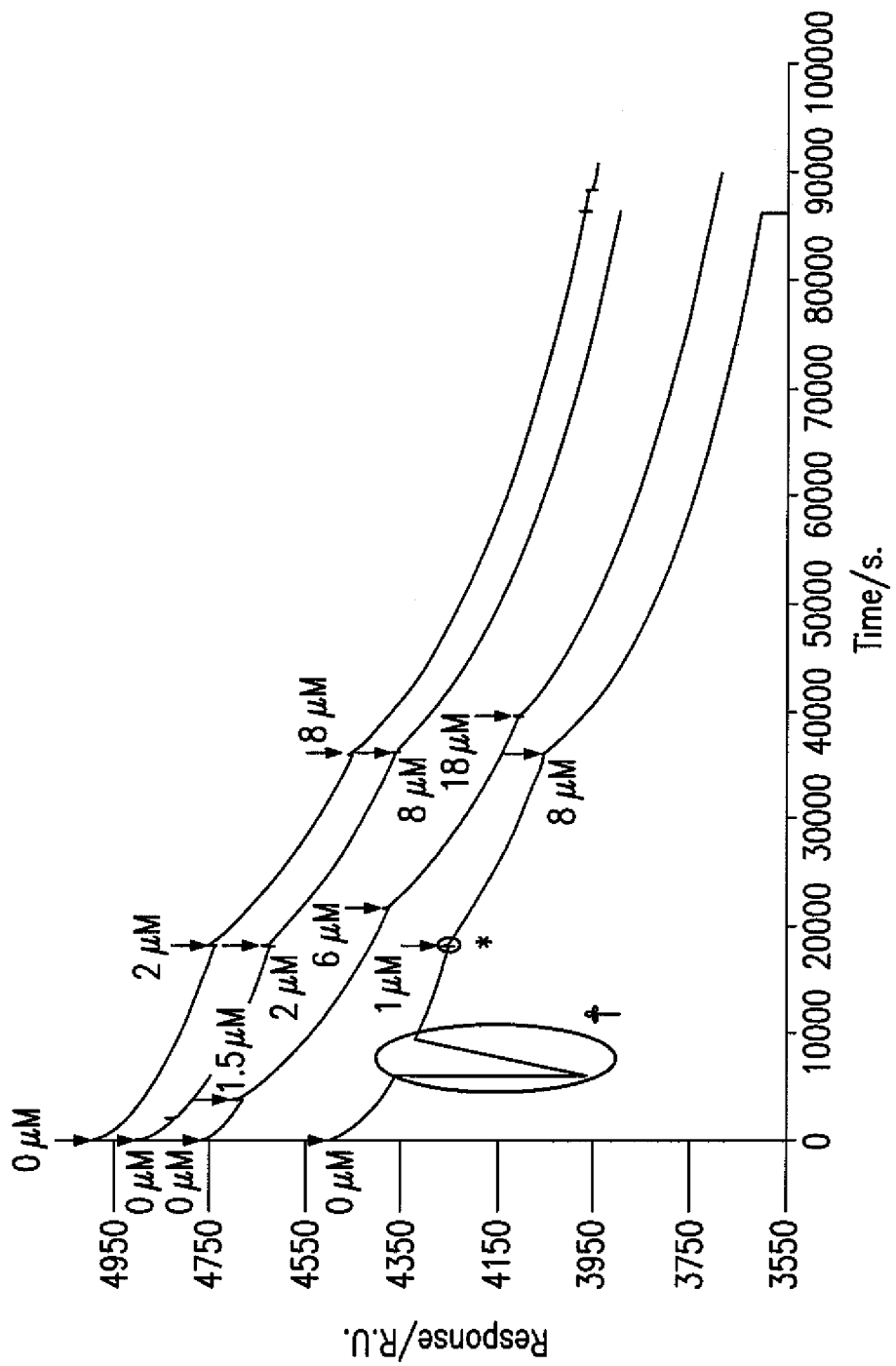
Figure 15B:
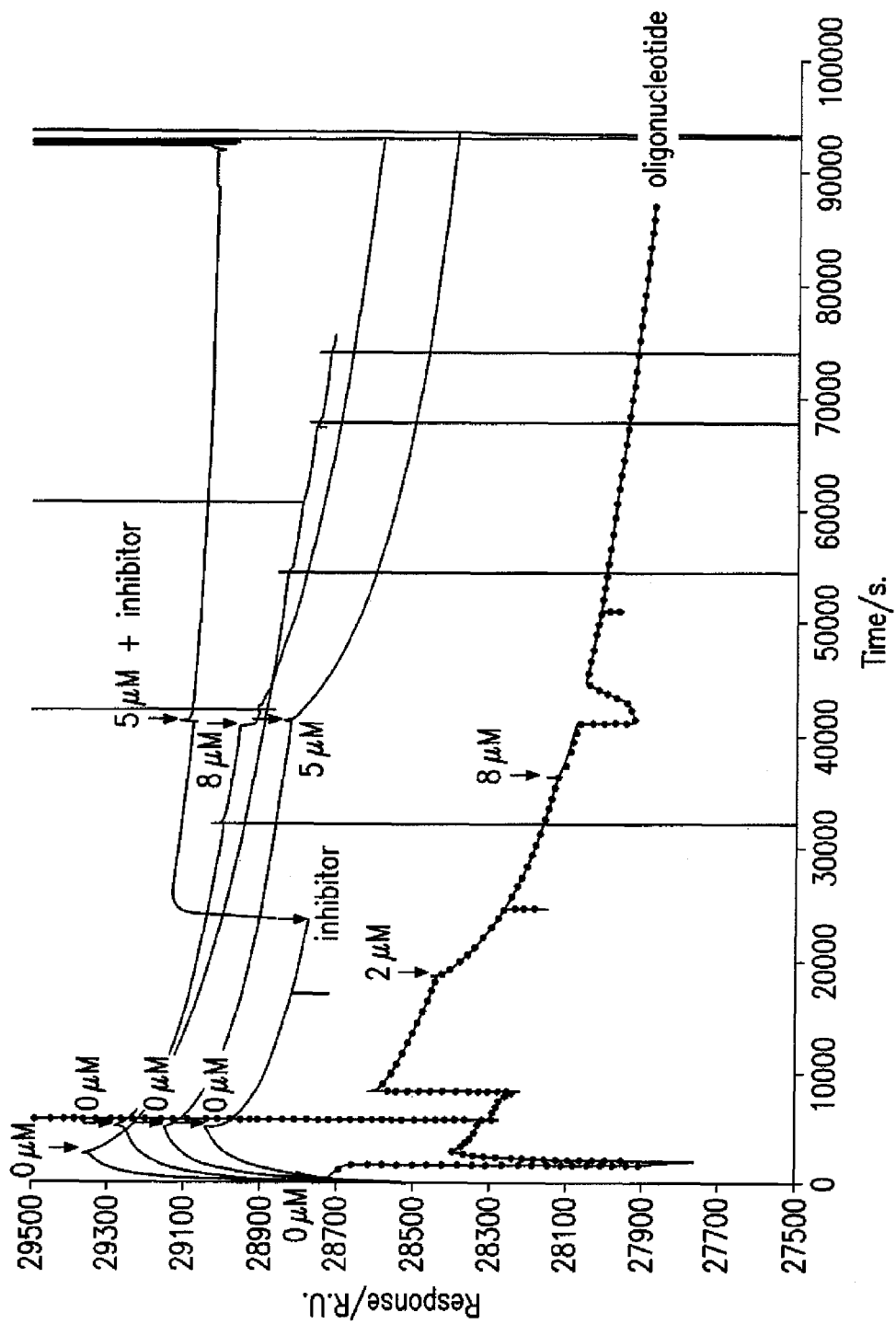

FIG. 15A-B. (A) Raw Biacore data (channel 2-channel 1) for all (continued in FIG. 15B) first derivative plots, showing dissociation of the insulin-oligonucleotide conjugate (5). Arrows (indicating start point) annotated with quinine concentration, refer to the quinine levels in the buffer being flowed over the surface of the chip. Note that small inset circle (*) highlights one example of spikes caused by a change of buffer. All such spikes were removed for the processing of the data; large inset circle (†) indicates a period of chip instability e.g. a bubble, such periods were also removed for the processing of the data. (B) Raw Biacore data (channel 2) continued.

Figure 16:
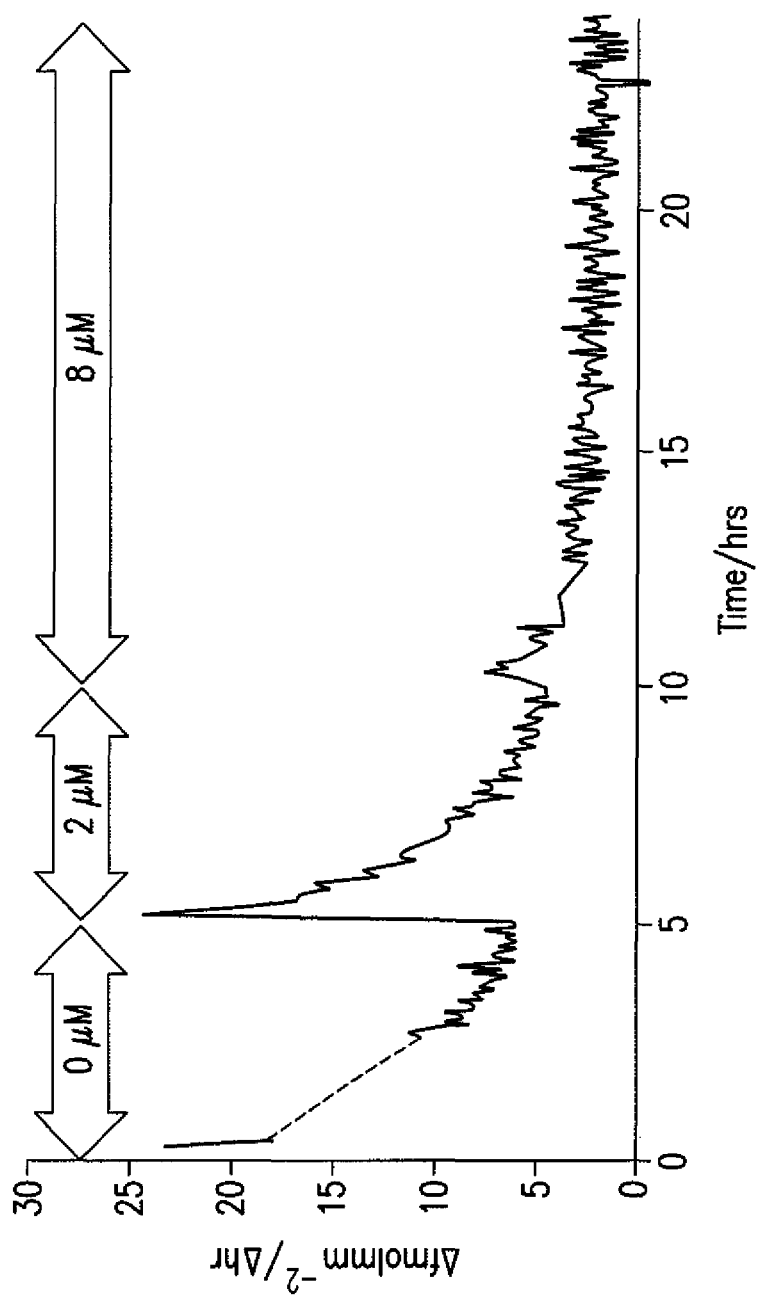

FIG. 16. Biacore results for release of oligonucleotide (i.e. no insulin attached)—first derivative plot which shows the amount of insulin-conjugate released per time period. μM concentrations refer to amount of quinine present. Dotted line indicates where data is absent due to chip instability during this time period (this trace is the first derivative ΔResponse Units/ΔTime to Δfmol mm$^{-2}$/Δhr, via 1000 RU=1 ng mm$^2$} of the dotted line in FIG. 15B).

Figure 17A:
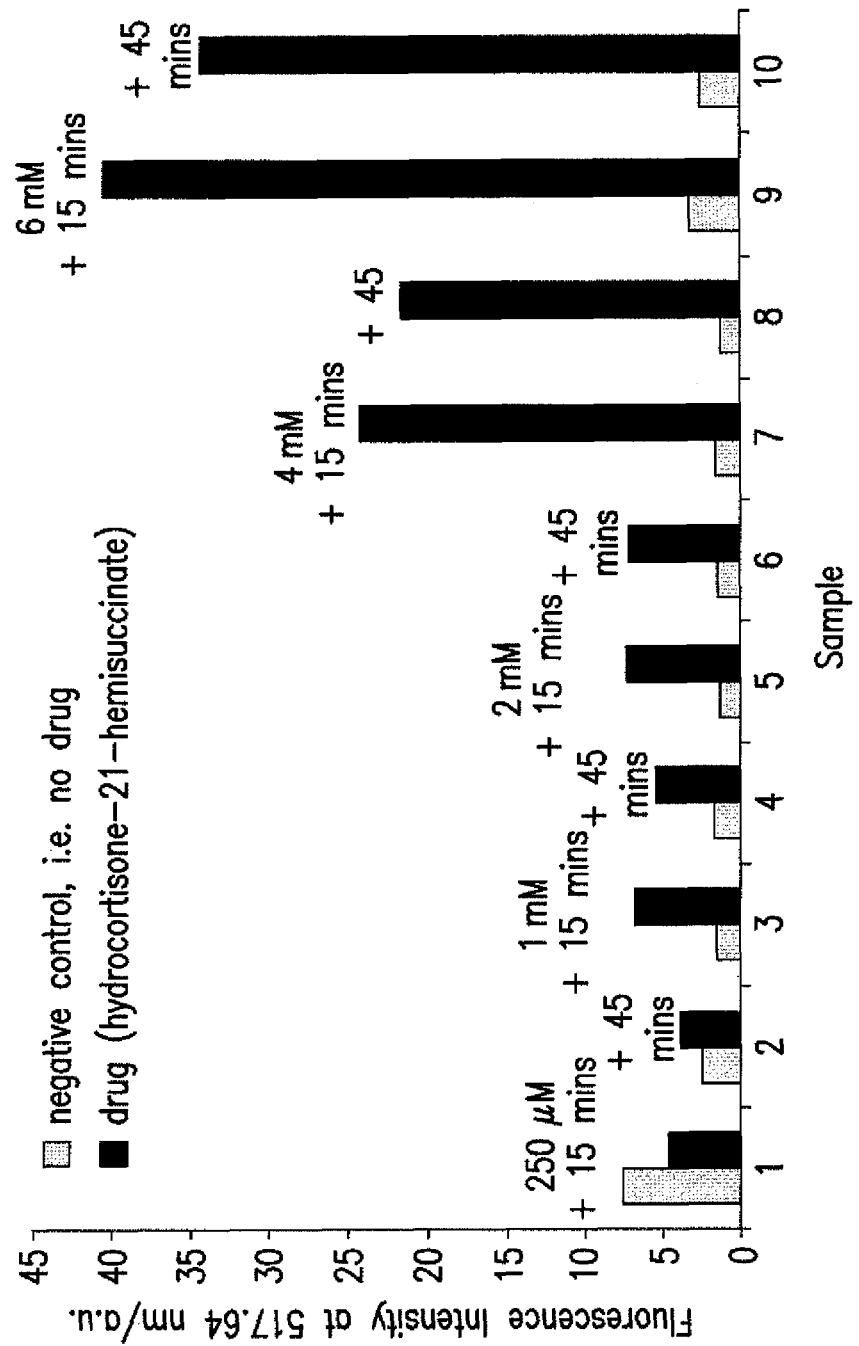
Figure 17B:
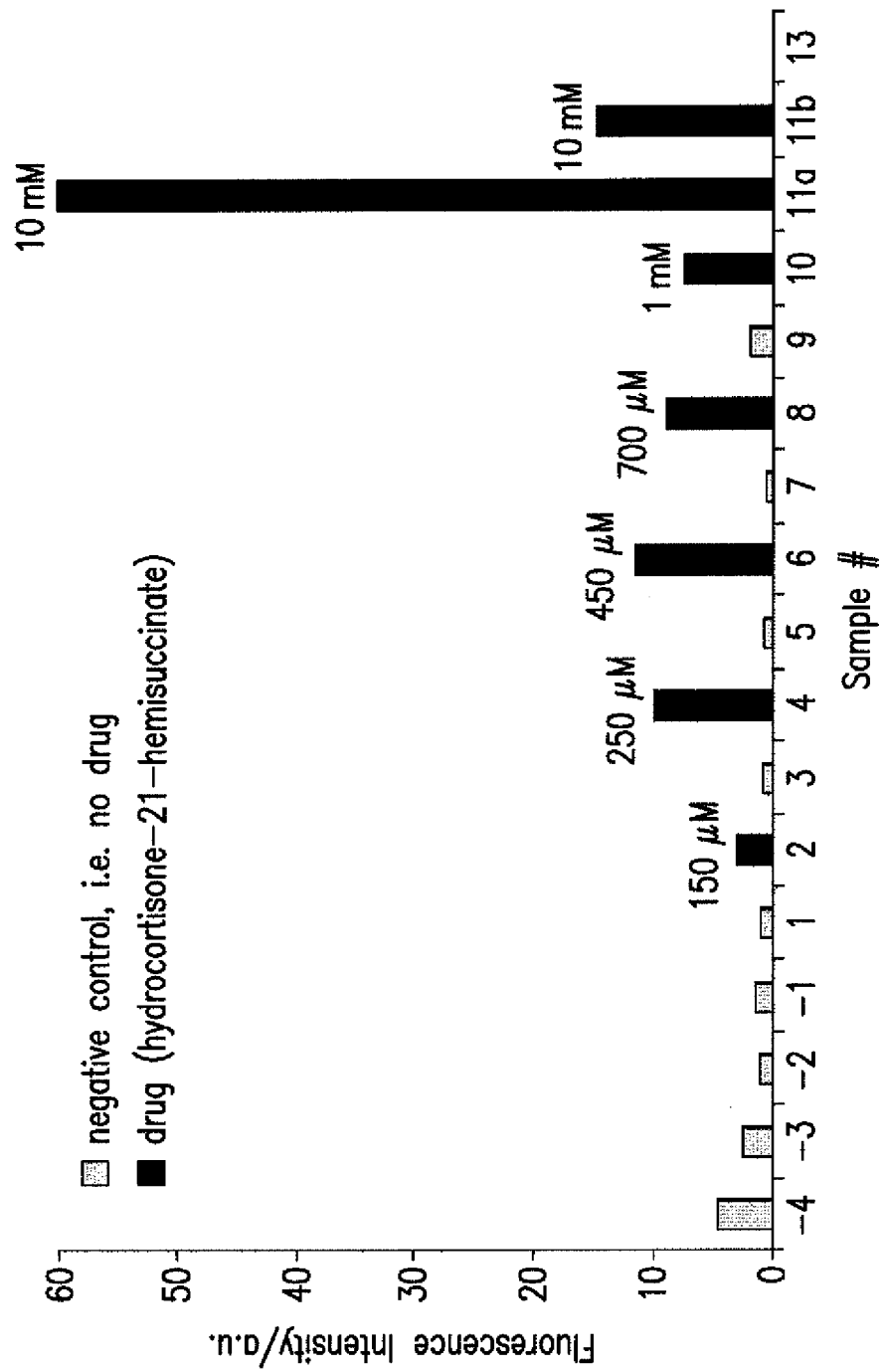

FIG. 17A-B. (A) Triggering of insulin conjugate release from microspheres using the corticosteroid hydrocortisone-21-hemisuccinate (HHS) occurs sluggishly at 250 μM, even after soaking for a total of 60 minutes (see sample 2—black bar, compared to no HSS—gray bar). At higher concentrations of HHS there is significant release of the conjugate. (B) Triggering of insulin conjugate release from microspheres using the (+)-cocaine (black bar—written above is the respective (+)-cocaine concentration in the sample; Gray bar—washes before or after cocaine added, i.e. contains no (+)-cocaine, note beads with insulin-oligonucleotide conjugate applied were washed two times after each addition of (+)-cocaine, then buffer added without the cocaine, followed by a 1 min soak, then the fluorescence of the sample measured. All washes and (+)-cocaine were added to the same set of conjugate coated beads in succession.

Figure 18:
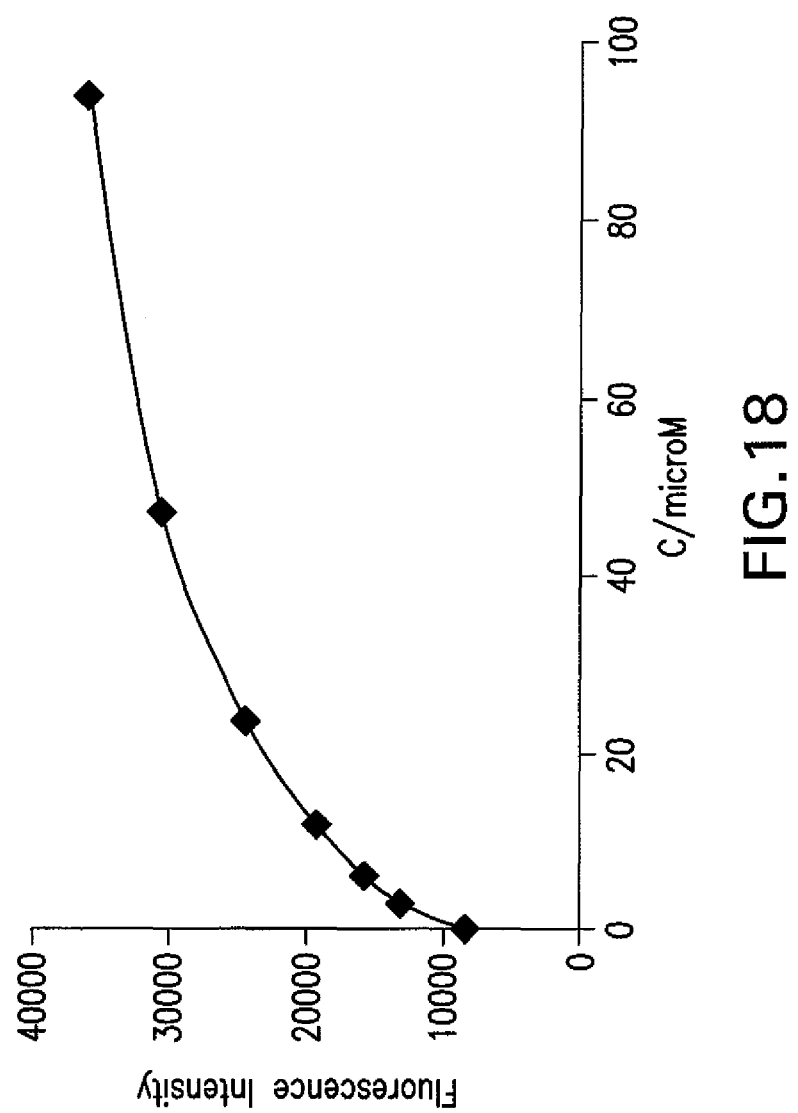

FIG. 18. Spiegelmer (L-MNS) binding of quinine. L-MNS, L-Q from ChemGenes (Wilmington, Mass.). Note that the sequence and label are same as mns-1, 1-Q, measurement conditions and concentrations were also the same (see FIG. 4, and Materials and Methods section in Example section 6). Spiegelmers were synthesized by using nuclease-resistant L-enantiomeric nucleotides.

Figure 19:
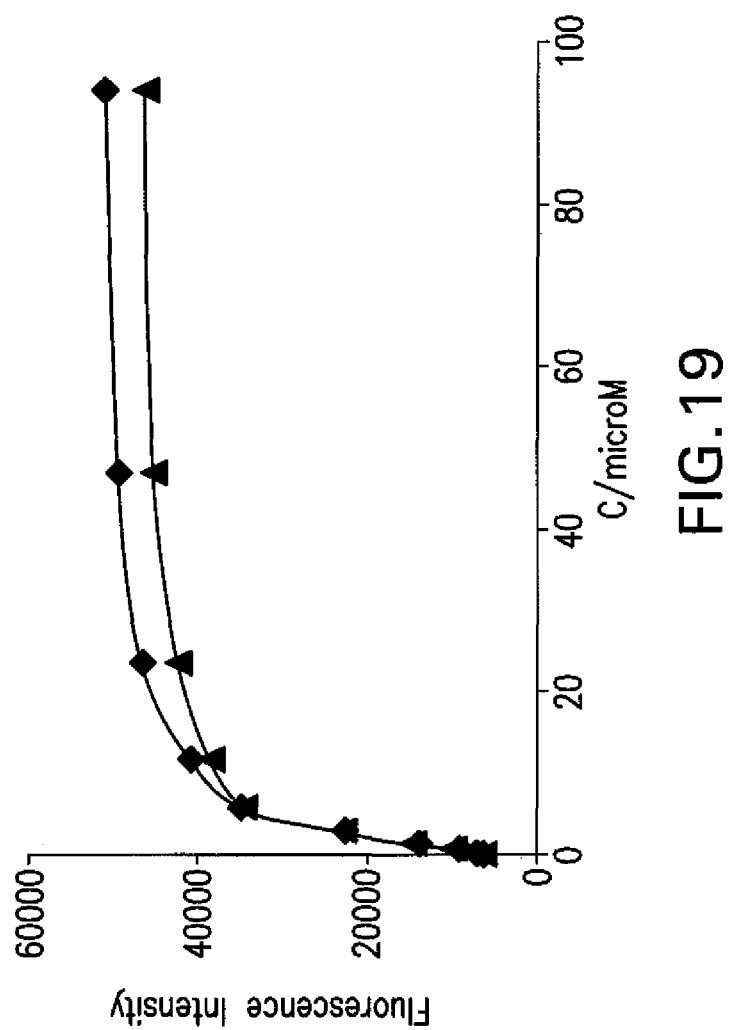

FIG. 19. MNS-1 binding of quinidine (▲) and quinine (♦).

SEQUENCE LISTING

The specification further incorporates by reference the Sequence Listing submitted herewith via EFS on Jan. 19, 2012. Pursuant to 37 C.F.R. §1.52(e)(5), the Sequence Listing text file, identified as 070050_4315_Seqlist.txt, is 3,839 bytes and was created on Jan. 19, 2012. The Sequence Listing, electronically filed herewith, does not extend beyond the scope of the specification and thus does not contain new matter.

5. DETAILED DESCRIPTION OF THE INVENTION

For clarity and not by way of limitation, the detailed description is divided into the following subsections:
(i) aptamer/drug conjugate complex;
(ii) triggers;
(iii) inhibitors;
(iv) administration; and
(v) methods of use.

5.1 Aptamer/Drug Conjugate Complex

The present invention provides for an aptamer complex comprising:
(i) a first trigger-binding oligonucleotide portion (hereafter, the "aptamer"); and
(ii) a second releasable oligonucleotide portion linked to a drug of interest (hereafter the "drug conjugate"); wherein the binding of the trigger compound releases the drug conjugate from the complex, preferably in a concentration-dependent manner.

The term "drug", as used herein, refers to a compound that is desirable to use in the body of an animal subject for a therapeutic and/or diagnostic purpose. Accordingly, the term "drug" encompasses, but is not limited to (i) conventional pharmaceutical compounds useful for the treatment of diseases or disorders, including, but not limited to, chemotherapeutic agents, anti-inflammatory agents, ionotropic agents, antimicrobial agents, etc.; and hormones; (ii) peptide, protein, and peptidomimetic compounds including, but not limited to cytokines, immunoglobulin molecules and fragments thereof, single chain antibodies, and toxins; as well as (iii) imaging agents such as detectable labels including but not limited to radioactive labels; paramagnetic labels, etc. In a specific non-limiting embodiment of the invention, the drug is insulin, which may be human insulin, porcine insulin, or a derivative thereof or an insulin analog (insulin receptor ligand) such as insulin lispro, insulin aspart, or insulin glulisine, and may be in monomeric or oligomeric form, such as, but not limited to dimeric, trimeric, tetrameric, pentameric, hexameric, heptameric, octameric, nonameric, decameric, undecameric, or dodecameric form or a mixture thereof (insulin has been observed to form oligomers in solution (and is stored as a hexamer in the pancreas), for example under fibril forming conditions including but not limited to pH 1.6 at 65° C. followed by cooling; see Sorci et al., 2009, Proteins 77(1):62-73; Chitta et al., 2006, J Am Soc Mass Spectrometry 17:1526-1534; Brange et al., 1993, Pharm. Biotech. 5:315-350; De Filippis et al., 2001, Crit. Rev. Therap. Drug Carrier Sys. 18:201-264; alternatively see United States Patent Application Publication 20090099064 (U.S. patent application Ser. No. 11/808,299)).

The drug conjugate comprises the drug and an oligonucleotide tether, optionally joined by a linker molecule. Linkage of the drug to the tether does not substantially diminish the activity of the drug (for example, the functional activity of the drug conjugate is at least about 50 percent, or at least about 60 percent, or at least about 70 percent, or at least about 80 percent, that of the unconjugated drug). Optionally, a linker molecule may be provided such that the oligonucleotide is enzymatically removed after the drug conjugate is released from the aptamer/drug conjugate complex. The oligonucleotide tether comprises a portion, preferably at least 6, or at least ten, or at least 15 nucleotides in length, which is at least about 80 percent, or at least about 90 percent or at least about 93 percent, or at least 98 percent or completely complementary to another region (hereafter, the hitching region) in the aptamer. The oligonucleotide tether may be between about 6 and 50 nucleotides and preferably between about 10 and 20 or between about 10 and 15 nucleotides in length. The oligonucleotide tether may comprise deoxyribonucleic acids and/or ribonucleic acids and may comprise atypical bases and/or linkages, for example phosphorothioate linkages. The site of linkage in the drug may be selected so as to minimally affect its activity. As a specific, non-limiting example, where insulin is the drug, linkage via the B1 Phe residue is preferred. Not by way of limitation, synthesis of an insulin drug conjugate may performed in four steps starting from human insulin: (i) the previously reported selective protection of the A1(Gly) e-amine and B29(Lys)-amine groups (Markussen et al., *J. Biol. Chem.* (1991), 266, 18814-18818); (ii) conjugation to the crosslinking agent NHS-PEO$_{12}$-maleimide, through the B1(Phe) e-amino group; (iii) deprotection of A1(Gly) e-amine and B29(Lys).-amine groups (Liu et al., *Bioconjugate Chem.* (1997), 8, 664-672); and (iv) coupling to the 5'-sulfahydryl modified oligonucleotide. Where the activity of the drug is not substantially affected by conjugation to the oligonucleotide, it is understood that providing drug conjugate is essentially equivalent to providing the (unconjugated) drug to a subject.

An aptamer, as that term is used herein, is an oligonucleotide consisting essentially of between about 30 and 150 nucleotides, preferably between about 40 and 100 nucleotides or between about 35 and 50 nucleotides, comprising a hitching region for the drug conjugate of interest. The aptamer may comprise deoxyribonucleaic acids and/or ribonucleic acids and may comprise atypical bases and/or linkages, for example phosphorothioate linkages. An aptamer of the invention may be designed or selected such that a complex forms between the aptamer and the drug conjugate, where the oligonucleotide tether of the drug conjugate is essentially annealed (optionally with some degree of imperfect matching) to the hitching region of the aptamer, and where the binding of a trigger to the aptamer/drug conjugate complex releases the drug conjugate.

In certain non-limiting embodiments, a known ligand/aptamer pair may be used as a starting point, and the oligonucleotide tether may be designed based on the sequence of the known aptamer. For example, a variety of such designed tethers may be tested for their ability, when comprised in a drug conjugate, to bind to the aptamer. It may then be determined whether binding of the ligand causes release of the drug conjugate (for example, using an affinity-based technique as discussed above). In such embodiments, it may be that the ligand originally identified does not have desirable properties of a trigger (see below), in which case a replacement trigger may be identified. Non-limiting examples include aptamers that bind cocaine (Stojanovic et al., *J. Am. Chem. Soc.* (2001), 123, 4928-4931), biotin (Wilson et al., *Biochemistry* (1998), 37, 14410-14419), vitamin B12 (Sussman et al., *Acta Crystallography* (1999), 55, 326-328), aminoglycoside (Cho et al., *Biochemistry*, (1998), 37, 4985-4992) and moenomycin A (Schurer et al., *Bioorg. Med. Chem.* (2001), 9, 2557-2563).

Alternatively, as a non-limiting example, an aptamer of the invention may be prepared by first preparing a drug conjugate comprising a drug of interest linked to an oligonucleotide tether, where said tether may comprise a natural or artificial sequence. Then, an aptamer may be prepared comprising a hitching region complementary (with optional mismatches, as discussed above) to at least a portion of the tether. For example, a hitching region may be designed based on the sequence of the oligonucleotide tether, and the remainder of the aptamer may be randomly or semi-randomly generated to form a library. From that library, molecules that stably (under the desired conditions) bind the drug conjugate may be selected, for example using an affinity-based separation technique such as affinity chromatography where the drug conjugate is the affinity ligand. Then, from selected aptamers that stably form an aptamer/drug conjugate complex, those aptamers may be selected (optionally in the form of aptamer/drug conjugate complexes) for the ability to bind a trigger, for example using an affinity technique where the trigger is the support-bound affinity ligand and/or where release of the drug conjugate is detected. As a non-limiting example of the latter, an affinity based separation technique where the aptamer is the affinity ligand may be applied in which detectably-labeled drug conjugate is added to support-bound aptamer under conditions which permit formation of the complex, then trigger is added and the amount of labeled drug conjugate released may be determined (alternatively, the aptamer could be detectably labeled and then complexed with support-bound drug conjugate, and the amount of labeled aptamer released by trigger could be measured).

An appropriate aptamer/drug conjugate may be developed using an in vitro evolution technique. See, for example, Lorsch and Szostak, *Nature* (1994), 371, 31-36; Kawazoe et al., *Nucl. Acids Symp. Ser.* (1999), 42, 177-178; Kawazoe et al., *Biomacromol.* (2001), 2, 681-686).

In particular, non-limiting examples, release of drug conjugate by trigger from the aptamer complex may be evaluated by release from a dextran matrix (SA-Chip, Biacore), under continuous flow, with surface plasmon resonance (SPR) monitoring, and/or by release from the surface of smooth beads (Bangs beads), with repetitions of buffer renewal after 30 minute soaks, followed by fluorescence monitoring (see Example Section 6, below). In either case an aptamer may be attached to the matrix or bead through biotin-streptavidin coupling at saturating concentrations, and then the surface may be loaded with drug conjugate. A Biacore SA chip, which is a surface consisting of a carboxymethylated dextran matrix pre-immobilized with streptavidin for binding of biotinylated molecules may be used. The length of the tether for binding to the hitching region then may be adjusted (by revision of the oligonucleotide tether) to get a basal rate of release (i.e., without trigger) and then concentration-dependent release by trigger to achieve desirable levels. For example, where insulin is the drug, the goal may be to obtain over 24 hours an insulin release profile that mimics the natural insulin release profile and that of a successful multiple injections approach to glycemic control (Polonsky et al., *J. Clin. Invest.* (1988), 81, 442-448).

In a specific, non-limiting embodiment of the invention, the aptamer comprises 5'-ATC TCG GGA CGA CAG GAT TTT CCT CAA TGA AGT GGG TCG TCC C-3' (SEQ ID NO:1) and the oligonucleotide tether comprises: 5'-GTC GTC CCG AGA T-3' (SEQ ID NO:2). In a related non-limiting embodiment, the drug conjugate is drug linked to the oligonucleotide tether comprising 5'-GTC GTC CCG AGA T-3' (SEQ ID NO:2). In one particular, non-limiting embodiment, the aptamer comprises 5'-ATC TCG GTC TCG GGA CGA CAG GAT TTT CCT CAA TGA AGT GGG TCG TCC CGA GA-3' (SEQ ID NO:12) and the oligonucleotide tether comprises 5'-GTC GTC CCG AGA CCG AGA T-3'(SEQ ID NO:13). For example, where the drug is insulin, the insulin conjugate may be 5'-GTC GTC CCG AGA CCG AGA T-3'-L$_1$-Insulin (SEQ ID NO:14) where L$_1$ is a linker. For example, in one specific non-limiting embodiment, the drug conjugate is 5'-GTC GTC CCG AGA CCG AGA T-PEO$_{12}$-insulin (SEQ ID NO:3). In another specific, non-limiting embodiment, the trigger for an aptamer having 5'-ATC TCG GGA CGA CAG GAT TTT CCT CAA TGA AGT GGG TCG TCC C-3' (SEQ ID NO:1) complexed with a drug-conjugate comprising an oligonucleotide tether comprising 5'-GTC GTC CCG AGA T-3' (SEQ ID NO:2) is quinine, and the drug may be insulin or another drug. In another specific, non-limiting embodiment, the trigger for an aptamer having 5'-ATC TCG GTC TCG GGA CGA CAG GAT TTT CCT CAA TGA AGT GGG TCG TCC CGA GA-3' (SEQ ID NO:12) complexed with a drug-conjugate comprising an oligonucleotide tether comprising 5'-GTC GTC CCG AGA CCG AGA T-3'(SEQ ID NO:13) is quinine, and the drug may be insulin or another drug. FIG. 4 shows a complex comprising oligonucleotides 5'-ATC TCG GGA CGA CAG GAT TTT CCT CAA TGA AGT GGG TCG TCC C-3' (SEQ ID NO:1) and 5'-GTC GTC CCG AGA T-3' (SEQ ID NO:2).

5.2 Triggers

As discussed above, a "trigger", as that term is used herein, is a molecule which results in the release of drug conjugate, preferably in a concentration-dependent manner. In certain embodiments, but not by way of limitation, a trigger may have one or more of the following characteristics"

i) the trigger is not commonly present in the environment of the subject in a form that makes it accessible to the aptamer/drug conjugate complex; for example, it is not typically found in food, minimizing chances for accidental release of drug conjugate;

ii) the trigger does not have a substantial physiological activity on its own (or, if it does, not substantial undesirable physiologic activity) in the concentration range used to trigger drug conjugate;

iii) the trigger desirably causes release at serum concentration readily achievable through its oral administration;

iv) interactions between the trigger and the aptamer/drug conjugate complex should be sufficiently selective to avoid accidental release of drug conjugate; and v) interactions between the trigger and the aptamer/drug conjugate should be adjustable to fit the actual therapeutic need (for example, the amount of drug conjugate released may be related to the concentration of trigger).

Where the drug is insulin, the pharmacokinetic profile of the trigger should be similar to that of glucose.

In a specific, non-limiting embodiment of the invention, the trigger is quinine.

In certain particular, non-limiting embodiments, the trigger may be a naturally occurring substance—for example wheat (e.g., wheat gluten), peanut allergen, milk (e.g. lactose), or a hormone (e.g. estrogen, progesterone, luteinizing hormone) and/or have its own substantial and optionally undesirable biological activity. As non-limiting examples of "natural" triggers, a pathogen or tumor antigen could inhibit the release of a conjugated cytokine, or a first hormone could trigger the release of a conjugated hormone the same as or different from the trigger, or histamine could result in the release of a conjugated anti-inflammatory agent.

For a given aptamer/drug conjugate complex, an appropriate trigger may be selected as set forth above, for example, by providing the aptamer bound to a support, loading the aptamer-support with detectable drug conjugate, and then, under conditions that resemble those desired for use in a subject, a test trigger may be supplied to the aptamer/drug conjugate complex, and the ability of the test trigger to cause the release of drug conjugate (particular in a concentration-dependent manner) may be determined. A test trigger which produces satisfactory results may then be considered in view of the desirable criteria set forth above.

For aptamer/trigger pairs known in the art, where the trigger may not manifest the desirable properties set forth above, a substitute trigger may be selected using the method described in the preceding paragraph. For example, but not by way of limitation, a substitute trigger may share structural characteristics with the trigger but manifest more desirable properties.

As a specific non-limiting example, but not by way of limitation, one suitable trigger is quinine. In a preferred non-limiting embodiment of the invention, the aptamer comprises 5'-ATC TCG GTC TCG GGA CGA CAG GAT TTT CCT CAA TGA AGT GGG TCG TCC CGA GA-3' (SEQ ID NO:12) and the oligonucleotide tether comprises 5'-GTC GTC CCG AGA CCG AGA T-3'(SEQ ID NO:13), and the trigger is quinine. In a specific non-limiting embodiment the drug is insulin, e.g. the drug conjugate is 5'-GTC GTC CCG AGA CCG AGA T-PEO$_{12}$-insulin (SEQ ID NO:3).

5.3 Inhibitors

The present invention further provides for an inhibitor which may be used to counteract the effect of the trigger and to inhibit release of the drug conjugate from the aptamer complex. While generally optional, where release of the drug conjugate may have serious clinical consequences such an inhibitor is very desirable. In one set of non-limiting embodiments, the inhibitor may be an oligonucleotide complementary to the sequence on the aptamer that is responsible for displacing the drug conjugate. In another set of non-limiting embodiments the inhibitor may form an inactivating complex with the trigger (e.g., but not by limitation, an antibody or fragment thereof, single chain antibody, receptor or receptor fragment, etc.).

5.4 Administration

In the practice of the present invention, an aptamer/drug conjugate is administered to a subject in a form and location to allow its availability to an intended trigger.

In certain non-limiting embodiments of the invention, an aptamer/drug conjugate complex may be administered to a subject in the absence of a linkage between said complex and a carrier substance. In such embodiments, the complex may be administered, for example, orally, intranasally, intraocularly, by pulmonary inhalation, intravenously, intraarterially, intrahepatically, intraperitoneally, rectally, cervically, vaginally, intravesically, intrathecally, subcutaneously, intramuscularly, etc.

In other non-limiting embodiments, an aptamer/drug conjugate may be linked to a carrier substance prior to administration to the subject. For example, the conjugate may be linked to a targeting molecule such as an antibody. Such targeted complexes may be administered, for example, orally, intranasally, intraocularly, by pulmonary inhalation, intravenously, intraarterially, intrahepatically, intraperitoneally, rectally, cervically, vaginally, intravesically, intrathecally, subcutaneously, intramuscularly, etc.

Alternatively, and not by way of limitation, an aptamer/drug conjugate may be incorporated into a polymeric matrix, A number of polymeric matrices are known in the art including, but not by way of limitation, polylactide polymers, polyglycolide polymers, poly(lactide-co-glycolide) polymers, polyanhydride polymers, polyorthoester polymers, the copolymer polifeprosan (a poly[bis(p-carboxyphenoxy)propane:sebacic acid copolymer (e.g. polifeprosan 20, where the poly[bis(p-carboxyphenoxy)propane:sebacic acid are in a molar ratio of 20:80). Such polymers, loaded with aptamer/drug conjugate complex, may be administered to a subject in the form of an implant which may be inserted into the body. In particular, non-limiting embodiments, the polymeric matrix may be DNA, for example applying the techniques of DNA nanotechnology so that the DNA matrix is comprised in a nanoparticle, and oligonucleotide aptamer/drug conjugate may be retained by said matrix by base pairing relationships between the DNA matrix and the oligonucleotide aptamer.

In other non-limiting embodiments, an aptamer/drug conjugate complex may be incorporated into a refillable depot device and inserted into an individual. As one non-limiting example, such a depot device may retain the complex in a particular location, for example, subcutaneously, within the central nervous system, intravaginally, intrautero, intraocularly or at the skin surface. Depending on the location, the depot device may be refilled, for example and not by way of limitation, by injection or by application of the complex to the device followed by reinsertion into the desired location. Non-limiting examples of refillable devices which may be used to administer therapeutic agents include the Ommaya reservoir, the iPort® injection portal (Patton Medical Devices, Austin, Tex.), a portal and reservoir for administration of ocular drugs (Lo et al., *Lab Chip* (2008), 8, 1027) and a portal and reservoir for administration of intraosseous drugs (Anderson, United States Patent Application Publication No. 20070003906). In certain non-limiting examples, the depot places the complex in communication with the patient's circulation, so that a trigger, carried by the blood, may access the complex in the depot.

5.5 Methods of Use

The present invention provides for a method of inducibly releasing a drug, comprising (i) providing an aptamer and a drug conjugate, wherein the aptamer and drug conjugate form a complex, and the drug may be released from the complex by binding of a trigger compound to the aptamer; and (ii) providing a trigger compound under conditions suitable for binding to the aptamer, wherein the trigger binds to the aptamer and releases the drug conjugate.

The present invention further provides for methods of administering a drug to a subject comprising introducing, into the subject, an aptamer and a drug conjugate, wherein the aptamer and drug conjugate form a complex, and the drug may be administered to the subject by a trigger compound (trigger) which releases the drug conjugate from the complex and makes the drug (either in the form of the drug conjugate or, where linkage between the drug and oligonucleotide tether is cleavable, as freed drug or a drug derivative) available to the subject.

A subject according to the invention is an animal and may be a human or a non-human subject. Non-limiting examples of non-human subjects include a mammal, a primate, a rodent, a livestock animal, a companion animal such as a dog or cat, a horse, a bird or a fish.

In certain non-limiting embodiments, the subject self-administers a trigger to elicit release of a drug. As non-limiting examples, a diabetic subject may administer a trigger that releases insulin conjugate prior to ingesting a meal; a glaucoma patient may administer a trigger that releases a miotic agent prior to entering a dark environment; and so forth. Desirably, the amount of drug conjugate release may be controlled by the amount of trigger administered.

A specific, non-limiting embodiment of the invention provides for a method of administering insulin to a subject, comprising introducing, into the subject, an aptamer and an insulin conjugate, wherein the aptamer and insulin conjugate form a complex, and the insulin may be administered to the subject by a trigger compound (trigger) which releases the insulin conjugate from the complex and makes the insulin available to the subject. Aptamer/insulin conjugate complex may be introduced into a subject desirably less frequently than the frequency of insulin injections associated with conventional therapy. Preferably, the amount of insulin conjugate released may be controlled by varying the amount of trigger administered, and release of insulin conjugate may preferably be inhibited by administration of an oligonucleotide inhibitor as described above. In a specific non-limiting embodiment, for an aptamer having 5'-ATC TCG GTC TCG GGA CGA CAG GAT TTT CCT CAA TGA AGT GGG TCG TCC GA-3' (SEQ ID NO:12) and a drug conjugate which is 5'-GTC GTC CCG AGA CCG AGA T-$PEO_{12}$-insulin (SEQ ID NO:3), quinine may be used as a trigger at a concentration range between about 0.1 and 44 μM serum concentration. Not by way of limitation, sufficient quinine may be self-administered (e.g., taken orally) to achieve a serum concentration of between about 0.2 and 1.5 μM to achieve suitable insulin release for a small meal, and sufficient quinine may be self-administered (e.g. taken orally) to achieve a serum concentration between about 1.6 and 4 μM to achieve suitable insulin release for a regular size meal. Further, the amount of quinine administered may depend on how many releases have been already carried out; for example if the subject has already released insulin conjugate for breakfast and lunch then to release enough insulin-conjugate for even a small dinner meal may require 8 microMolar. Conversely, a large breakfast may only need a small amount of quinine (1 microMolar) if it is the first time a release has been triggered.

6. EXAMPLE

Triggered Release of an Active Peptide Conjugate from a DNA Device by an Orally Administratable Small Molecule 6.1 Materials and Methods Abbreviations:

DI, diboc-insulin moiety; $PEO_{12}$, dodeca(ethyleneoxide) linker; M, maleimide moiety; a.u., arbitary units; iSp18, 18-atom hexaethylene glycol spacer; 5BioTEG, 5' biotin with tetraethylene glycol spacer.

Screening.

Oligonucleotides MNS-1 and 1-Q were custom-made and HPLC purified by Integrated DNA Technologies, Inc (Coralville, Iowa, USA) and were used as received. The base sequence for MNS-1 is: 5'-fluorescein-ATC TCG GGA CGA CAG GAT TTT CCT CAA TGA AGT GGG TCG TCC C (SEQ ID NO:4), and 1-Q is: 5'-GTC GTC CCG AGA T-dabcyl (SEQ ID NO:5). All compounds (except cocaine) were purchased from Sigma-Aldrich Co. (St. Louis, Mo., USA). All measurements were performed in 20 mM Tris-HCl pH 7.4, 140 mM NaCl, 5 mM KCl, 2 mM $MgCl_2$. Mixture of MNS-1 and 1-Q was incubated for 5 min at room temperature, then a series of standard dilutions of all compounds were added to the mixture solutions of MNS-1 and 1-Q to final concentrations of 50 nM and 150 nM respectively. Measurements were performed after an incubation time of 30 min. The measurements were performed on a Perkin-Elmer Victor II microplate reader (Wallac, Finland) with a 485-nm excitation filter and a 535-nm emission filter.

Insulin Conjugate Synthetic Summary.

Synthesis was performed in four steps starting from human insulin: 1) the previously reported selective protection of the A1(Gly) ε-amine and B29(Lys) γ-amine groups (Markussen et al., *J. Biol. Chem.* (1991), 266, 18814-18818); 2) conjugation to the crosslinking agent NHS-$PEO_{12}$-maleimide, through the B1(Phe) ε-amino group; 3) deprotection of A1(Gly) ε-amine and B29(Lys) γ-amine groups (Liu et al., *Bioconjugate Chem.* (1997), 8, 664-672); 4) coupling to the 5'-sulfahydryl modified oligonucleotide.

Insulin-$PEO_{12}$-Malemide (4).

A freshly prepared solution of NHS-$PEO_{12}$-maleimide linker (Pierce) (790 μL, 15.8 μmoles, 20 mM in anhydrous DMSO (Acros)) was combined, in a siliconized-microcentrifuge tube, with solid diboc-insulin (2) (Markussen et al., *J. Biol. Chem.* (1991), 266, 18814-18818) (47.5 mg, 7.91 μmoles). The resulting clear solution was stood overnight in the dark at room temperature. The solvent was removed and the resulting residue dried (in vacuo). Removal of the two t-Boc protecting groups was carried out by addition 1 mL of ice cold (0° C.) TFA (Acros), containing 5-10% anisole (Acros), to the diboc-insulin-$PEO_{12}$-maleimide (3) residue under an argon atmosphere (Liu et al., *Bioconjugate Chem.* (1997), 8, 664-672). After 10 minutes, (periodic and brief sonication can be used to get all of the starting material in to solution if needed) the reaction was stopped by evaporation of the TFA under a stream of argon. The resulting residue was dried in vacuo and purified by reverse phase HPLC to give (4) in 29% yield as determined by reverse phase HPLC, with HPLC peak identities verified by mass spectroscopy, m/z 6558.82 (calculated for $[MH]^+$: 6559.4).

Insulin-$PEO_{12}$-Oligonucleotide (5).

Activation of the sulfhydryl-oligonucletide was carried out according to a modified procedure based on the protocol provided with the "ReduceImm™ Immobilized Reductant Column" (Pierce, Catalog No. 77701, Lot No. HJ108860). The column was equilibrated to room temperature. The storage solution was poured off, and then the column washed with 5 mL of "Buffer 1" (0.1 M sodium phosphate, 1 mM EDTA, pH 8.0). The column was then activated by washing with 10 mL of freshly prepared 10 mM DTT solution (prepared by dissolving 15 mg of DTT in 10 mL of "Buffer 1"). The activating DTT was then removed by washing the column with 5 mL of "Buffer 1" followed by 5 mL of PBSE at pH 6.8.

100 uL (100 nmoles) of $C_3H_7$—S—S-TAG AGC CAG AGC CCT GCT G-FAM (SEQ ID NO:6) (IDT) (1 mM in water) was added to 900 µL of PBSE buffer, and the resultant 1 mL solution flowed on to the activated column. The column was then capped and incubated at room temperature for about 70 minutes hour. The column was washed with 5 mL of PBSE and the incubated for a further 30 minutes. The sulfhydryl-oligonucleotide was eluted from the column in 1 mL increments using PBSE-PLUS at pH 6.8 (PBSE with a NaCl concentration of 1 M) with the bulk of the product eluting in the third milliliter, and most of the remainder found in the fourth milliliter. The third milliliter fraction was concentrated to about half volume, to 585 µL, using a Centricon centrifugal filter device (MWCO 3000, Cat. No. 4202, Lot No. L6DN7971). The recovered yield from fraction 3, after concentration, was 48.4 nmoles, as determined by absorbance at 260 nm.

The activated oligonucleotide was added to insulin-$PEO_{12}$-maleimide (3.19 mg, 485 nmoles, in 100 µL of PBSE buffer) and stood overnight in the dark at room temperature. The resulting insulin-oligonucleotide conjugate was purified by reverse phase HPLC resulting in (5) in 56% yield as determined by peak integration. The identity was confirmed by mass spectroscopy, m/z 13,063.5 (calculated for $[M]^+$:13,063.7).

Biacore.

For SPR experiments, Biacore X system and commercially available Biacore SA sensor chips from Biacore AB (Uppsala, Sweden) were used.

Preparation of Matrix-Displaying Aptamers.

A 1 µM solution of aptamer aptamer 5'-/5BioTEG//iSp18//iSp18/ATC TCG GTC TCG GGA CGA CAG GAT TTT CCT CAA TGA AGT GGG TCG TCC CGA GA (SEQ ID NO:11) in 10 mM HEPES at pH 7.4, 150 mM NaCl, and 3 mM EDTA (in HBS-EP) was applied to one of the SA sensor chip's two channels for 20 min at 4 µL $min^{-1}$, followed by a 120 sec wash with 4 M urea/15 mM EDTA to remove any nonspecifically adsorbed material. The aptamer used for these SPR experiments was shorter by two bases relative to the aptamer used in the microsphere experiments (see SEQ ID NO:7). According to the Biacore SA chip literature, the matrix was a highly irregular 3D dextran hydrogel recognition matrix with a height of approximately 100-200 nm and an uneven distribution of streptavidin. The matrix was coated with biotinylated aptamer containing two 18-atom hexaethylene glycol spacers between the biotin and the oligonucleotide. On the basis of changes in SPR response, the aptamer was coated at saturation densities of 0.12-to-0.15 pmol $mm^{-2}$, an estimated average inter-aptamer distance of 10-to-11 nm (based on a 100 nm height for the dextran layer. 1.2-to-1.6 molecules of insulin-conjugate bound per aptamer on initial loading, with oligonucleotide binding (i.e. no insulin attached) at 1.2 per aptamer. Where possible, the channel with no aptamer or insulin-conjugate/oligonucleotide deposited acted as a blank for correction of system influence. When the additional channel was not able to be used as a blank, data for the first 10 minutes of any buffer change was omitted due to artifacts occurring in this time period caused by washes with the new buffer.

Matrix-Aptamer Hybridization with (5). (5) 1 µM in NaCl (140 mM), KCl (5 mM), and $MgCl_2$ (1.2 mM), buffered to pH 7.4 with Tris (20 mM), was dispensed on the aptamer displaying channel at 1 µL $min^{-1}$ until saturation (80 min), with the other channel used as a system influence control when possible. Monitoring of conjugate (5) release was taken 15 minutes after the end of the conjugate (5) application time to allow for weak non-specifically bound conjugate to be washed from the surface. Conjugate dissociation in real time was measured through the decrease in mass, again using the formula 1000 R.U.=1 ng $mm^2$. In some experiments, instrumental instabilities were observed as occasional spikes in sensorgrams during long-time monitoring. Such spikes were manually removed, a procedure that does not influence any of the values reported herein.

Tissue Culture and Insulin Signaling Assay.

McA-RH7777, rat hepatoma cells were grown in DMEM media with 20% fetal bovine serum. Cells were incubated in serum-free medium for 5 hours and treated with insulin and insulin-oligonucleotide conjugate at the concentration of 100 nM for 10 min. Cell lysates were prepared in SDS lysis buffer (2% SDS, 62.5 mM Tris HCL (pH 6.8), 10% glycerol, 50 mM DTT, 0.01% Bromophenol Blue). All antibodies were purchased from Cell Signaling Technology (Danvers, Mass.).

Characterization of Insulin-$PEO_{12}$-Oligonucleotide (5).

The isolated product (4) displayed a mass spectral parental ion peak at m/z 6558.82 (calculated for $[MH]^+$: 6559.4) consistent with a one-to-one insulin-linker (4) conjugate, see FIG. 8B. The isolated product (5) gave a mass spectral ion peak at m/z 13,063.5 (calculated for $[M]^+$:13,063.7). UV-vis and florescence spectroscopy showed an absorption maximum and emission maximum at 495 and 520 nm respectively, consistent with the presence of fluorescein. Also the conjugate displayed a band at 260 nm consistent with the presence of DNA with a 260 nm/280 nm ratio of 1.80, consistent with the presence of the aromatic amino acid residues of the insulin.

Aptamer Functionalized Microspheres.

(for a biotin binding site:aptamer ratio of 5:1) Streptavidin functionalized magnetic microspheres (Bangs Laboratories), 2 mL, were washed with HEPES 10 mM/NaCl 150 mM/pH 7.4 buffer 3×2 mL, using a magnet to separate out the microspheres from the washings. The microspheres were suspended in 1 mL of the same buffer. The aptamer 5'-/5BioTEG//iSp18//iSp18/ATC TCG GTC TCG GGA CGA CAG GAT TTT CCT CAA TGA AGT GGG TCG TCC CGA GAC C-3' (SEQ ID NO:7) (IDT, Coralville, Iowa, USA), 2 nmoles, was dissolved in 10 mL of the buffer and added slowly drop-wise to the microsphere suspension under continuous shaking. The mixture was incubated for one hour and then washed 3×, once with a 1 mL volume then twice with 200

μL volumes after transfer to a 1.5 mL microcentrifuge tube. The washed microspheres were resuspended in 1 mL of buffer and stored at 4° C. until use. For a biotin binding site:aptamer ratio of 1:1, i.e. saturated, 800 μL of microspheres were prepared as above, with the exception that they were resuspended in 400 uL of buffer with 8 nmoles of aptamer then added.

Hybridization of Insulin-$PEO_{12}$-Oligonucleotide and Aptamer Functionalized Microspheres.

Aptamer functionalized microspheres (200 uL containing 0.4 nmoles of aptamer were washed 1×200 μL of binding buffer and then resuspended in 100 μl of the same buffer. The insulin-$PEO_{12}$-oligonucleotide conjugate in 0.5 nmoles, in 37 μL of water, was added to the suspension and incubated, with constant mixing by inversion, overnight at room temperature, protected from light.

Quinine Triggered Release of (5) from Aptamer Coated Microspheres.

All release experiments were carried out in water containing NaCl (140 mM), KCl (5 mM), and $MgCl_2$ (1.2 mM), buffered to pH 7.4 with Tris (20 mM). Streptavidin coated microspheres were mixed with biotinylated aptamer to obtain aptamer coated microspheres, see above for detailed preparation. The aptamer was hybridized with (5) to form the Watson-Crick base pairs shown in FIG. 1A, left hand side. The release profiles of insulin-conjugate (5) from microspheres were shown in FIG. 12A-B. Exposure of the aptamer coated microspheres to twenty percent excess of (5) resulted in fifty-to-eighty percent of (5) being taken up from solution. With continued renewal of the microsphere suspension buffer, the microspheres slowly released (5), as shown by the dotted traces in FIG. 12A-B. On addition of two micromolar quinine (see solid traces in FIG. 12A-B), a pulse of (5) was released (as supported by size exclusion chromatography, see FIG. 13), tailing over approximately three hours. On addition of six micromolar quinine at three and one half hours an additional pulse with analogous characteristics of the first pulse was observed. A third analogous pulse can be triggered using eighteen micromolar quinine. Very similar release profiles were observed for concentrated and five-fold dilution of the aptamer, an average insulin-insulin spacing of 4 and 8 nm respectively. Also, the system gave a similar release profile on heating the assembly for ten minutes at 70° C. prior to incubation at room temperature overnight compared to only incubation at room temperature. However, under the same conditions, the release of the oligonucleotide (without insulin attached) released more facilely, as shown by FIG. 12B (trace marked with X's).

MALDI-TOF Analysis.

The mass of insulin derivatives (excluding the final insulin-oligonucleotide conjugate—see FIG. 10) were determined by MALDI-TOF mass spectrometry. Samples were mixed 1:5 (v/v) with a matrix solution of sinapinic acid (10 mg/mL) in 50% acetonitrile/0.1% trifluoroacetic acid, spotted on the sample plate, and allowed to dry. A standard solution of 6 mM apomyoglobin was mixed with matrix and spotted in the same way for use as a calibrant.

Spectra were acquired on a Voyager-DE Pro (Applied Biosystems, Foster City, Calif.) operating in linear mode. Instrument settings were as follows: accelerating voltage, 25000V; grid voltage, 93%; extraction delay time, 200 ns; laser intensity 1700-2000.

HPLC.

For HPLC purification a Shimadzu LC-6AD pump equipped with an SPD-M10A PDA detector was used. Insulin derivatives were purified by reverse phase chromatography on a SymmetryPrep™ C18 7 μm, 19×150 mm column, (Waters), unless stated otherwise. See respective traces and figures for mobile phase details 6.2 Results and Discussion The new approach to therapeutic peptide delivery (FIG. 1A) hinges, among other things, on the identification of a small molecule trigger-triggerable device pair ("D" and "i", respectively, in FIG. 1A), such that: 1) the small molecule is not commonly present in food, minimizing chances for accidental hypoglycemic events; 2) the small molecule must have negligible physiological activity on its own at the escalating concentrations used to trigger multiple releases—the increases in concentrations are required in order to allow for identical pulses (if required) over several administrations of the small molecule (it is for this reason that a glucose aptamer would be useless); 3) the small molecule should trigger release at serum concentrations readily achievable through its oral administration; 4) interactions between the device and the small molecule have to be sufficiently selective, to avoid accidental release resulting in hypoglycemia; 5) interactions between the device and the small molecule have to be adjustable to fit the actual therapeutic need; and 6) the patient should be able to inhibit the release, should he/she change his/her mind about a meal or in the case of accidental overdose of the small molecule.

Oligonucleotide-based receptors or aptamers that bind small molecules provided an alternative approach and fulfil all six requirements listed above. Several "proof-of-principle" DNA devices for triggered release of active forms of proteins (e.g., thrombin or Taq polymerase) from their complexes with inhibitors (Dittmer et al., *Angew. Chem. Int. Ed.* (2004), 43, 3550-3553; Kolpashchikov and Stojanovic, *J. Am. Chem. Soc.* (2005), 127, 11348-11351) have been demonstrated, but these devices had too rapid $k_{off}$ rates for practical applications. Instead, in order to achieve precise control of the release rate, the release of oligonucleotide-insulin conjugates from their "structure-switching" complexes (Nutiu and Li, *J. Am. Chem. Soc.* (2003), 125, 4771-4778; Liu and Lu, Angew. Chem. Int. Ed. (2006), 45, 90-94) with DNA receptors was focused. Importantly, such release can be stopped through administration of an oligonucleotide complementary to the sequence on the aptamer that is responsible for displacing the oligonucleotide-insulin conjugate (iii in FIG. 1A) (Rusconi et al., *Nature* (2002), 419, 90-94). Cross-linking of polymers with antibody-antigen pairs, with circulating antigens disrupting the crosslinks, has been previously proposed for triggered release (Miyata et al., *Nature* (1999), 399, 766-769), and a similar principle has been recently applied with a structure switching aptamers (Tang et al., *J. Am. Chem. Soc.* (2008), 130, 11268-11269).

FDA-approved drugs were screened for their ability to interact with a mismatched DNA-based three-way junction previously reported to bind cocaine and steroids (at concentrations above those typically achievable in serum (Stojanovic et al., *J. Am. Chem. Soc.* (2000), 122, 11547-11548; Green et al., *J. Am. Chem. Soc.* (2006), 128, 15278-15282). The screening was performed at the low concentrations required for negligible physiological activity in order to identify a molecule with high selectivity (FIG. 1B). A screening assay was used that is based on the fluorescein labeled cocaine aptamer and a competitor oligonucleotide with a DABCYL quencher (see Materials and Methods). A suitable compound—quinine. ($K_d$~0.6 μM) was identified. Quinine was used to provide a characteristic bitter taste in tonic water and was also used as an orally administrable therapeutic agent for malaria, with rapid absorption, and a recommended serum therapeutic concentration range of 14-to-46 μM (Franke et al., *Eur. J. Clin. Pharmocol.* (1987), 33, 293-296). Quinine also bound to the spiegelmer of the aptamer (see figures, and Materials and Methods), opening a possibility to use completely DNAse-stable oligonucleotide devices.

An insulin-oligonucleotide conjugate suitable for release from the aptamer was synthesized. The B1(Phe) 8-amino group position was selected to attach the oligonucleotide and a spacer, based on previous activity studies on PEG conjugates (Hinds and Kim, Adv. Drug Delivery. Rev. (2002), 54, 505-530; Uchio et al., *Adv. Drug Delivery. Rev.* (1999), 35, 289-306). The synthesis was performed in three steps starting from boc protected A1(Gly) 8-amine and B29(Lys) γ-amine human insulin (Markussen et al., *J. Biol. Chem.* (1991), 266, 18814-18818), as depicted in FIG. 2A. The final product was confirmed by mass spectroscopy (See figures, and Materials and Methods for full synthesis and characterization details). Finally, the full activity of the insulin conjugate was confirmed in rat hepatoma cells (FIG. 2B, and Materials and Methods).

Release of the insulin-conjugate (i→ii in FIG. 1A) was studied in two different systems: 1) release from a dextran matrix (SA-Chip, Biacore), under continuous flow, with surface plasmon resonance (SPR) monitoring, and 2) release from the surface of non-porous beads followed by fluorescence monitoring. In both cases, the quinine sensor oligonucleotide was attached to the surface through biotin-streptavidin coupling at saturating concentrations, and then loaded the surface with insulin conjugate. Comparable results were obtained in both systems, and the SPR results were discussed herein (bead results are presented in FIG. 12A-B). The biotinylated quinine sensor oligonucleotide was deposited on a Biacore SA chip, which was a surface consisting of a carboxymethylated detran matrix pre-immobilized with streptavidin for binding of biotinylated molecules. Then, through several iterations the number of bases in the sensor oligonucleotide and insulin-conjugate were adjusted, to be able to mimic a typical daily pattern of insulin secretion for three meals; that was, a basal rate of release (i.e., without quinine) over 24 hours, combined with a three pulses of quinine induced release at 5 hour intervals. The system was non-responsive to other hydrophobic molecule (including cocaine and steroids) at concentrations far exceeding those realistically found in serum (see figures, and Materials and Methods).

Mimicking the normal insulin release profile (Duckworth, et al., *Angew. Chem. Int. Ed.* (2007), 46, 8819-8822; Wang et al., *Bioelectron.* (2007), 22, 1798-1806) was focused, while amounts of quinine that are readily achievable with oral ingestion being used (FIG. 3D). For example, the desired profile with three postprandial boluses (e.g., breakfast, lunch, and dinner) by using quinine at escalating concentrations of 0 µM, 2 µM, and 8 µM (FIG. 3A), or, after pre-washing the chip, using 1.5, 6, and 18 µM was accomplished. The chip could be reloaded with insulin conjugate, obtaining reproducible results (FIG. 3A—dotted-line trace).

Figure 3A:
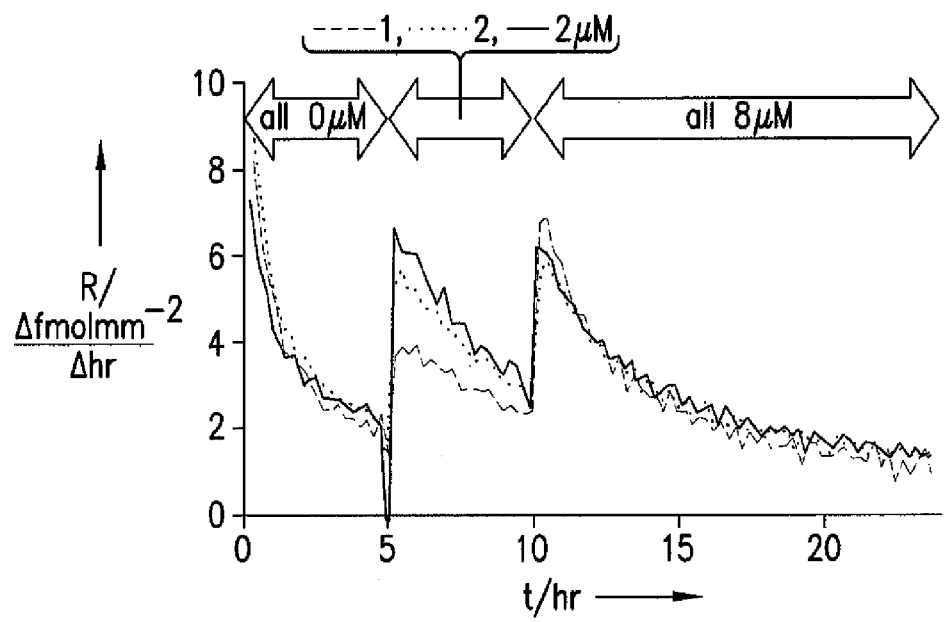
Figure 3B:
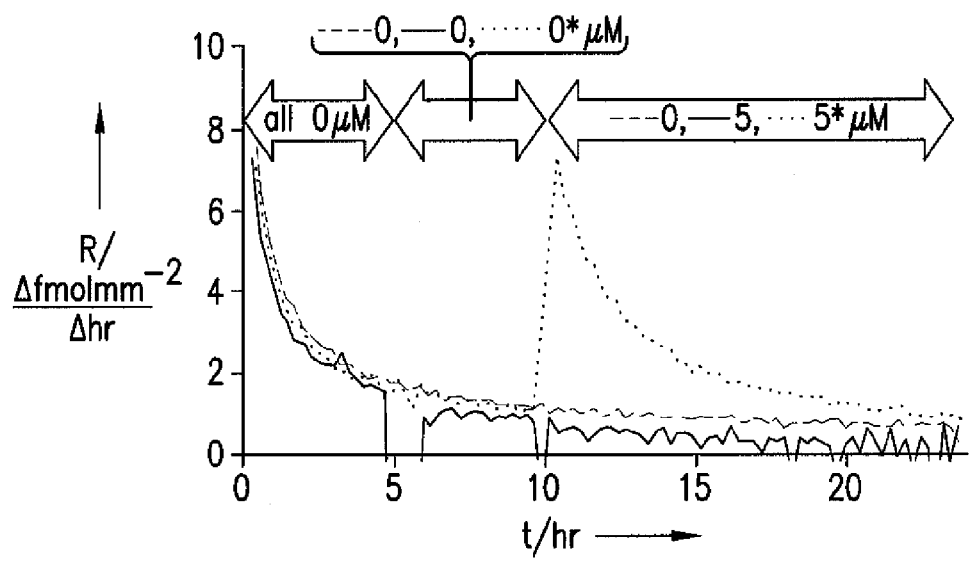
Figure 3C:
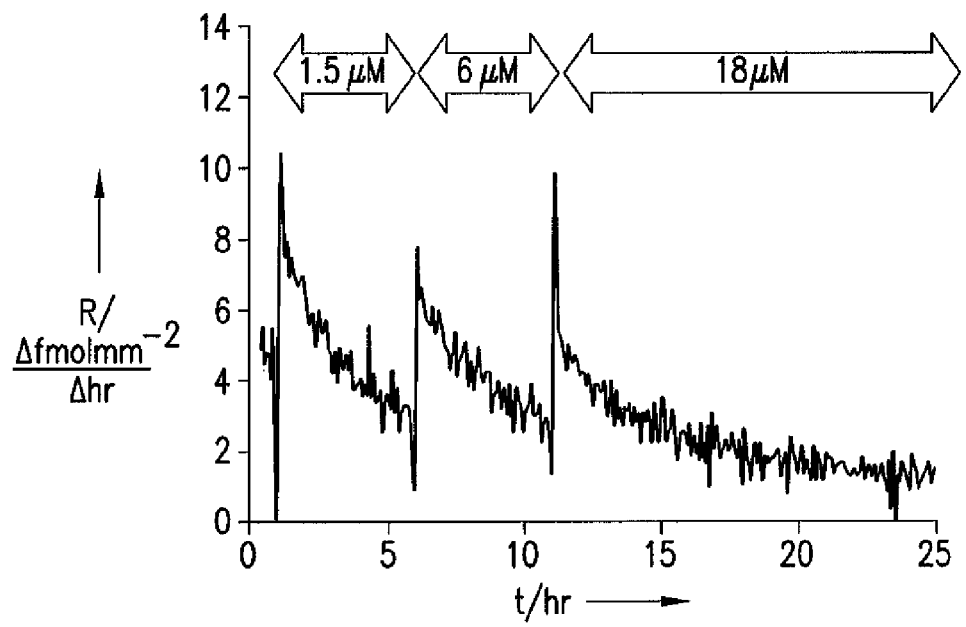
Figure 3D:
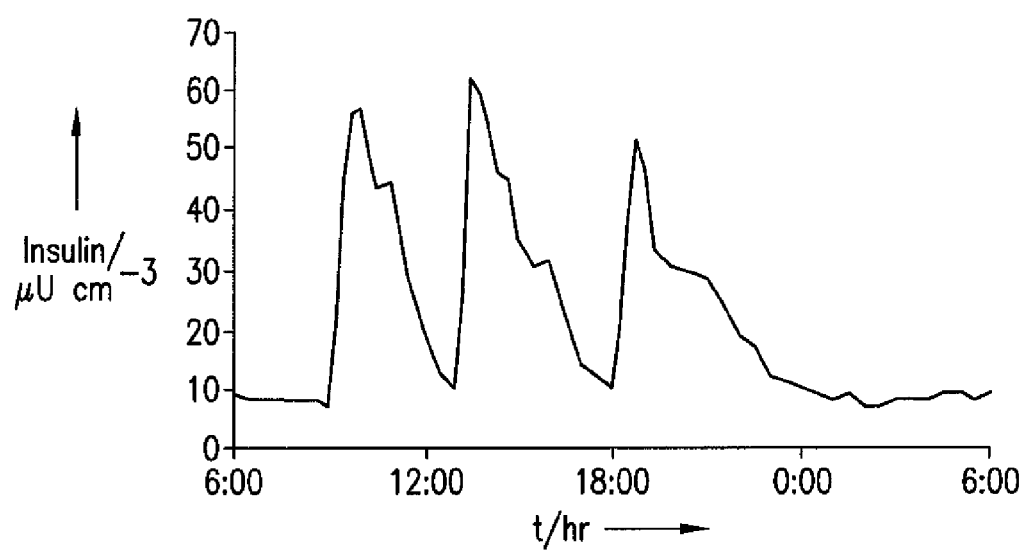

FIG. 3 has also shown that the amount of insulin conjugate released for "lunch" could be controlled by adjusting quinine concentration: 0 µM quinine was used for a missed lunch scenario (FIG. 3B, dotted-line trace); 1 µM quinine was used for a small lunch scenario (FIG. 3A, dashed-line trace); with 2 µM quinine used for a "standard" lunch scenario (FIG. 3A, solid-line and dotted-line traces). It was also demonstrated that if a hypoglycemic event was threatening, an oligonucleotide inhibitor (Miyata et al., *Nature* (1999), 399, 766-769) strand could be used to block the release of the insulin-conjugate in the presence of quinine, as shown in FIG. 3B—solid-line trace (compared with dotted-line trace).

In conclusion, harmless (subtherapeutic) concentrations of an orally administrable small molecule were used to release an active form of a peptide drug from a supporting matrix. Most importantly, a complex release profile was readily achieved that matched a challenging therapeutic need. These results were significant for several reasons: 1) it was demonstrated that in vitro the feasibility of multiple injections being substituted by an orally-triggered release from a depot, with release profiles that mimicked those required to achieve good glycemic control, and that could be otherwise obtained only through a complex regimen; 2) the described principle was general, and it could be used with other small molecules for which aptamers can be isolated and for other peptides that retain their activity as conjugates (Duckworth et al., *Angew. Chem. Int. Ed.* (2007), 46, 8819-8822; Wang et al., *Biosens. Bioelectron.* (2007), 22, 1798-1806); 3) the described DNA device was the first of its kind that moved proof-of-concept to a relevant peptide and a relevant small molecule, with a realistic potential for practical applications; 4) it was demonstrated that the insulin-oligonucleotide conjugate retained its activity, which opened up the various possibilities to formulate oligomeric forms of insulin, and to control their retention and activity through DNA nanotechnology approaches. In vivo success would depend on integrating the DNA device with suitable biologically compatible functionalized polymers.

Various references are cited herein, the contents of which are hereby incorporated by reference in their entireties.

We claim:

1. An aptamer complex comprising:
   (i) a first trigger-binding oligonucleotide portion comprising the sequence of SEQ ID NO:12; and
   (ii) a drug conjugate comprising a second releasable oligonucleotide portion comprising the sequence of SEQ ID NO: 2 or SEQ ID NO: 13 linked to a drug selected from the group consisting of a pharmaceutical compound, a peptide, a protein, a peptidomimetic compound, and an imaging agent;
   wherein the binding of a trigger compound releases the drug conjugate from the complex, and
   wherein the trigger compound is selected from the group consisting of quinine and quinidine.

2. The complex of claim 1, wherein the drug is selected from the group consisting of a chemotherapeutic agent, an anti-inflammatory agent, an ionotropic agent, an antimicrobial agent, a hormone, a cytokine, an immunoglobulin molecule or fragment thereof a single chain antibody, a toxin; a radioactive label and a paramagnetic label.

3. The complex of claim 1, wherein the second releasable oligonucleotide portion comprises the sequence 5'-GTC GTC CCG AGA CCG AGA T-3'(SEQ ID NO:13).

4. The complex of claim 1 wherein the drug is insulin or an insulin analog.

5. The complex of claim 3 wherein the drug is insulin or an insulin analog.

6. The complex of claim 1 wherein the drug conjugate is 5'-GTC GTC CCG AGA CCG AGA T-PEO12-insulin (SEQ ID NO:3).

7. A method of inducibly releasing a drug conjugate, comprising
   (i) providing an aptamer and a drug conjugate, wherein the aptamer and drug conjugate form a complex, wherein the complex comprises
      (a) a first trigger-binding oligonucleotide portion comprising the sequence of SEQ ID NO:12; and
      (b) a drug conjugate comprising a second releasable oligonucleotide portion comprising the sequence of SEQ ID NO: 2 or SEQ ID NO: 13 linked to a drug selected from the group consisting of a pharmaceutical compound, a peptide, a protein, a peptidomimetic compound, and an imaging agent;
      wherein the drug conjugate may be released from the complex by binding of a trigger compound to the aptamer; and
   (ii) providing a trigger compound under conditions suitable for binding to the aptamer, wherein the trigger binds to the aptamer and releases the drug conjugate, and wherein the trigger compound is selected from the group consisting of quinine and quinidine.

8. The method of claim 7, wherein the drug is selected from the group consisting of a chemotherapeutic agent, an anti-inflammatory agent, an ionotropic agent, an antimicrobial agent, a hormone, a cytokine, an immunoglobulin molecule or fragment thereof, a single chain antibody, a toxin; a radioactive label and a paramagnetic label.

9. The method of claim 7, wherein the drug is insulin or an insulin analog.

10. The method of claim 7, wherein the second releasable oligonucleotide portion comprises the sequence 5'-GTC GTC CCG AGA CCG AGA T-3'(SEQ ID NO:13).

11. The method of claim 10, wherein the drug is insulin or an insulin analog.

12. The method of claim 7, wherein the drug conjugate is 5'-GTC GTC CCG AGA CCG AGA T-PEO$_{12}$-insulin (SEQ ID NO:3).

13. A method of administering a drug to a subject comprising
(i) introducing into the subject, an aptamer and a drug conjugate, wherein the aptamer and drug conjugate form a complex, wherein the complex comprises
(a) a first trigger-binding oligonucleotide portion comprising the sequence of SEQ ID NO:12; and
(b) a drug conjugate comprising a second releasable oligonucleotide portion comprising the sequence of SEQ ID NO: 2 or SEQ ID NO: 13 linked to a drug selected from the group consisting of a pharmaceutical compound, a peptide, a protein, a peptidomimetic compound, and an imaging agent;
wherein the drug conjugate may be released from the complex by binding of a trigger compound to the aptamer; and
(ii) administering a trigger compound selected from the group consisting of quinine and quinidine to the subject, wherein the trigger binds to the aptamer and releases the drug conjugate from the complex, and wherein the availability of the drug conjugate provides the drug to the subject.

14. The method of claim 13, wherein the drug is selected from the group consisting of a chemotherapeutic agent, an anti-inflammatory agent, an ionotropic agent, an antimicrobial agent, a hormone, a cytokine, an immunoglobulin molecule or fragment thereof, a single chain antibody, a toxin; a radioactive label and a paramagnetic label.

15. The method of claim 13, wherein the drug is insulin or an insulin analog.

16. The method of claim 13, wherein the second releasable oligonucleotide portion comprises the sequence 5'-GTC GTC CCG AGA CCG AGA T-3'(SEQ ID NO:13).

17. The method of claim 16, wherein the drug is insulin or an insulin analog.

18. The method of claim 13, wherein the drug conjugate is 5'-GTC GTC CCG AGA CCG AGA T-PEO$_{12}$-insulin (SEQ ID NO:3).

* * * * *

SEQUENCE LISTING

```
<160> NUMBER OF SEQ ID NOS: 14

<210> SEQ ID NO 1
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 1
atctcgggac gacaggattt tcctcaatga agtgggtcgt ccc                         43

<210> SEQ ID NO 2
<211> LENGTH: 13
<212> TYPE: DNA
<213> ORGANISM: Artificial sequence
```

```
<220> FEATURE:
<223> OTHER INFORMATION: Synthetic oligonucleotide

<400> SEQUENCE: 2
gtcgtcccga gat                                                        13

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (19)..(19)
<223> OTHER INFORMATION: PEO12-insulin

<400> SEQUENCE: 3
gtcgtcccga gaccgagat                                                  19

<210> SEQ ID NO 4
<211> LENGTH: 43
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(1)
<223> OTHER INFORMATION: fluorescein

<400> SEQUENCE: 4
atctcgggac gacaggattt tcctcaatga agtgggtcgt ccc                       43

<210> SEQ ID NO 5
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (13)..(13)
<223> OTHER INFORMATION: dabcyl

<400> SEQUENCE: 5
gtcgtcccga gat                                                        13

<210> SEQ ID NO 6
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(1)
<223> OTHER INFORMATION: C3H7-S-S
<220> FEATURE:
<221> NAME/KEY: Unsure
<222> LOCATION: (19)..(19)
<223> OTHER INFORMATION: FAM

<400> SEQUENCE: 6
tagagccaga gccctgctg                                                  19

<210> SEQ ID NO 7
<211> LENGTH: 55
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(1)
<223> OTHER INFORMATION: /5BioTEG//iSp18//iSp18/

<400> SEQUENCE: 7
atctcggtct cgggacgaca ggatttcct caatgaagtg ggtcgtcccg agacc    55

<210> SEQ ID NO 8
<211> LENGTH: 53
<212> TYPE: DNA
<213> ORGANISM: Artificial sequence
<220> FEATURE:
<223> OTHER INFORMATION: Synthetic oligonucleptide
<220> FEATURE:
<221> NAME/KEY: Unsure
<222> LOCATION: (1)..(1)
<223> OTHER INFORMATION: Matrix-L2

<400> SEQUENCE: 8
atctcggtct cgggacgaca ggatttcct caatgaagtg ggtcgtcccg aga    53

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(1)
<223> OTHER INFORMATION: Fluorescein
<220> FEATURE:
<221> NAME/KEY: Unsure
<222> LOCATION: (19)..(19)
<223> OTHER INFORMATION: L1-Insulin

<400> SEQUENCE: 9
gtcgtcccga gaccgagat    19

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 10
tctcgggacg acccacttca ttg    23

<210> SEQ ID NO 11
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(1)
<223> OTHER INFORMATION: /5BioTEG//iSp18//iSp18/

<400> SEQUENCE: 11
atctcggtct cgggacgaca ggatttcct caatgaagtg ggtcgtcccg aga    53

<210> SEQ ID NO 12
<211> LENGTH: 53
```

```
<212> TYPE: DNA
<213> ORGANISM: Artificial sequence
<220> FEATURE:
<223> OTHER INFORMATION: Synthetic oligonucleotide

<400> SEQUENCE: 12
atctcggtct cgggacgaca ggattttcct caatgaagtg ggtcgtcccg aga    53

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
gtcgtcccga gaccgagat    19

<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (19)..(19)
<223> OTHER INFORMATION: L1-Insulin

<400> SEQUENCE: 14
gtcgtcccga gaccgagat    19
```